US010080776B2

(12) United States Patent
Torigoe et al.

(10) Patent No.: US 10,080,776 B2
(45) Date of Patent: Sep. 25, 2018

(54) MOLECULAR MARKER FOR CANCER STEM CELL

(71) Applicants: Sapporo Medical University, Sapporo-shi, Hokkaido (JP); Sumitomo Dainippon Pharma Co., Ltd., Osaka-shi, Osaka (JP)

(72) Inventors: Toshihiko Torigoe, Sapporo (JP); Yoshihiko Hirohashi, Sapporo (JP); Noriyuki Satoh, Sapporo (JP); Kenjiro Kamiguchi, Sapporo (JP); Rena Morita, Sapporo (JP); Satoshi Nishizawa, Sapporo (JP); Akari Takahashi, Sapporo (JP)

(73) Assignees: Sapporo Medical University, Sapporo-shi, Hokkaido (JP); Sumitomo Dainippon Pharma Co., Ltd., Osaka-shi, Osaka (JP)

( * ) Notice: Subject to any disclaimer, the term of this patent is extended or adjusted under 35 U.S.C. 154(b) by 0 days.

(21) Appl. No.: 15/162,833

(22) Filed: May 24, 2016

(65) Prior Publication Data
US 2016/0367628 A1 Dec. 22, 2016

Related U.S. Application Data

(62) Division of application No. 13/967,410, filed on Aug. 15, 2013, now Pat. No. 9,399,760, which is a division of application No. 13/126,039, filed as application No. PCT/JP2009/005676 on Oct. 27, 2009, now Pat. No. 8,541,544.

(30) Foreign Application Priority Data

Oct. 27, 2008 (JP) .................................. 2008-275539
Mar. 19, 2009 (JP) .................................. 2009-068656

(51) Int. Cl.
*A61K 38/17* (2006.01)
*C12N 15/113* (2010.01)
*C12Q 1/6886* (2018.01)
*G01N 33/50* (2006.01)
*G01N 33/574* (2006.01)
*C07K 7/06* (2006.01)
*C12N 5/0783* (2010.01)

(52) U.S. Cl.
CPC .............. *A61K 38/177* (2013.01); *C07K 7/06* (2013.01); *C12N 5/0638* (2013.01); *C12N 15/113* (2013.01); *C12N 15/1138* (2013.01); *C12Q 1/6886* (2013.01); *G01N 33/5017* (2013.01); *G01N 33/574* (2013.01); *G01N 33/57492* (2013.01); *C12N 2310/14* (2013.01); *C12Q 2600/112* (2013.01); *C12Q 2600/118* (2013.01); *C12Q 2600/136* (2013.01); *C12Q 2600/158* (2013.01); *G01N 2333/705* (2013.01)

(58) Field of Classification Search
None
See application file for complete search history.

(56) References Cited

U.S. PATENT DOCUMENTS

| 7,358,231 B1 * | 4/2008 | McCaffey .......... C07K 14/4748 |
| | | 435/7.1 |
| 8,541,544 B2 | 9/2013 | Torigoe et al. |
| 9,399,760 B2 | 7/2016 | Torigoe et al. |
| 2008/0166340 A1 | 7/2008 | Tureci et al. |
| 2011/0135640 A1 | 6/2011 | Tureci et al. |
| 2013/0280166 A1 | 10/2013 | Tureci et al. |

FOREIGN PATENT DOCUMENTS

| JP | 2007-506417 A | 3/2007 |
| WO | WO200157276 | * 11/2001 |
| WO | WO 2002/083921 A2 | 10/2002 |
| WO | WO200283921 | * 10/2002 |
| WO | WO 2004/005883 A2 | 1/2004 |
| WO | WO 2007/012811 A2 | 2/2007 |
| WO | WO 2007/132883 A1 | 11/2007 |
| WO | WO 2008/091908 A2 | 7/2008 |
| WO | WO 2008/127100 A1 | 10/2008 |
| WO | WO 2009/036246 A2 | 3/2009 |

OTHER PUBLICATIONS

Harig et al (Blood, vol. 98, p. 2999-3005, 2001 (Year: 2001).*
Genbank Submission; NCBI, Accession No. NM_003106; Chakravarthy et al.; Sep. 14, 2008.
Genbank Submission; NCBI, Accession No. NM_030663; Yatsenko et al.; Feb. 11, 2008.
Genbank Submission; NCBI, Accession No. NM_153330; Ohtsuka et al.; Mar. 30, 2008.
Genbank Submission; NCBI, Accession No. NM_198944; Grimwood et al.; Dec. 9, 2007.
Asanuma et al., Basaloid-type breast cancer stem cell marker at high frequency. Proceedings of the Japanese Society of Pathology. Mar. 20, 2009;98(1):220.

(Continued)

*Primary Examiner* — Lei Yao
(74) *Attorney, Agent, or Firm* — Wolf, Greenfield & Sacks, P.C.

(57) ABSTRACT

A molecular marker for detecting a cancer stem cell in a cell mass which is a subject of interest, wherein the molecular marker can be detected in a cancer stem cell contained in the subject of interest but cannot be detected in a normal cell and a cancer cell that is different from a cancer stem cell; a method for determining the presence or absence of a cancer stem cell in a subject of interest by using the molecular marker as an measure; a kit for determining the presence or absence of a cancer stem cell, which comprises at least a reagent for detecting the molecular marker; a polypeptide encoded by the molecular marker; an antibody capable of recognizing an epitope of an expression product of a gene derived from the molecular marker; a nucleic acid capable of inhibiting the expression of the molecular marker; and a nucleic acid vaccine comprising a gene derived from the molecular marker.

3 Claims, 25 Drawing Sheets
Specification includes a Sequence Listing.

(56) References Cited

OTHER PUBLICATIONS

Asanuma et al., Frequent expression of stem cell marker in basaloid breast cancer. Dai 67 Kai Proceedings of the Japanese Cancer Association. Sep. 30, 2008. p. 177. Abstract P-2043.

Chiou et al., Positive correlations of Oct-4 and Nanog in oral cancer stem-like cells and high-grade oral squamous cell carcinoma. Clin Cancer Res. Jul. 1, 2008;14(13):4085-95.

Durzynski et al., Olfactory-like receptor cDNAs are present in human lingual cDNA libraries. Biochem Biophys Res Commun. Jul. 22, 2005;333(1):264-72.

Fan et al., Medulloblastoma stem cells. J Clin Oncol. Jun. 10, 2008;26(17):2821-7.

Harig et al., Induction of cytotoxic T-cell responses against immunoglobulin V region-derived peptides modified at human leukocyte antigen-A2 binding residues. Blood. Nov. 15, 2001;98(10):2999-3005.

Hirohashi et al., An analysis of cancer stem cell antigen molecule SOX2. Proceedings of the Japanese Society of Pathology. Mar. 20, 2009;98(1):255.

Hirohashi et al., Immunological evaluation of the lung cancer stem cells. Dai 67 Kai Proceedings of the Japanese Cancer Association. Sep. 30, 2008. pp. 439-440. Abstract P-8239.

Kakarala et al., Implications of the cancer stem-cell hypothesis for breast cancer prevention and therapy. J Clin Oncol. Jun. 10, 2008;26(17):2813-20.

Kamiguchi et al., The role of novel molecular chaperone DNAJB8 in centrosome. Proceedings of the Japanese Society of Pathology. Feb. 5, 2007;96(1):168.

Kenkichi, A study on the investigation of the role of cancer stem cells in solid tumor and the development of targeting therapy against cancer stem cells. Annual Report of Cancer Research. Ministry of Health, Labour and Welfare. 2007, Sep. 2008, National Cancer Center. p. 373-377.

Kubo et al. Definition of specific peptide motifs for four major HLA-A alleles. J Immunol. Apr. 15, 1994;152(8):3913-24.

Lee et al., Pancreatic cancer stem cells. Journal of Clinical Oncology. Jun. 10, 2008;26(17):2806-2812.

Malnic et al., The human olfactory receptor gene family. Proc Natl Acad Sci U S A. Feb. 24, 2004;101(8):2584-9. Erratum in: Proc Natl Acad Sci U S A. May 4, 2004;101(18):7205.

Morita et al., Heat shock protein DNAJB8 is a novel target for immunotherapy of colon cancer-initiating cells. Cancer Sci. Apr. 2014;105(4):389-95. doi:10.1111/cas.12362.

Nakatsugawa et al., SOX2 as a cancer stem cell antigen molecule. Abstracts of the 12th General Meeting of Society for Fundamental Cancer Immunology.. Jun. 13, 2008. p. 39.

Nishizawa et al., HSP DNAJB8 controls tumor-initiating ability in renal cancer stem-like cells. Cancer Res. Jun. 1, 2012;72(11):2844-54. doi: 10.1158/0008-5472.CAN-11-3062.

Nishizawa et al., Novel cancer-testis antigen, DNAJB8 is expressed preferentially in cancer initiating cells. The 13th Annual Meeting of Japanese Society of Cancer Immunology Shorokushu . May 20, 2009. p. 74.

Nishizawa et al., Novel cancer-testis antigen, DNAJB8 is expressed preferentially in cancer initiating cells. Dai 68 Kai Proceedings of the Japanese Cancer Association. 2009. p. 294. Abstract P-0579.

Peacock et al., Cancer stem cells and the ontogeny of lung cancer. Journal of Clinical Oncology. Jun. 10, 2008;26(17):2883-2889.

Sato et al., Identification and analysis of a novel molecular chaperone DNAJB8. Proceedings of the Japanese Society of Pathology. Mar. 18, 2006;95(1):390.

Sato et al., Immune responses against tumor antigens expressed in human cancer stem cells. Dai 67 Kai Proceedings of the Japanese Cancer Association. Sep. 30, 2008. p. 82. Abstract S12-3.

Sato et al., Perspective of human cancer immunotherapy. Dai 67 Kai Proceedings of the Japanese Cancer Association. Sep. 30, 2008. p. 460. Abstract ML20.

Schmitz et al., Identification of SOX2 as a novel glioma-associated antigen and potential target for T cell-based immunotherapy. Br J Cancer. Apr. 23, 2007;96(8):1293-301.

Takahashi et al., Cancer stem cell antigen SOX2 for breast cancer and pulmonary cancer. Hokkaido Ihou, Program of the 88th Hokkaido Medical Congress. Sep. 1, 2008. pp. 17.

Takahashi et al., Exploration of cancer stem cell tumor antigens from lung cancer, breast cancer and sarcoma. Dai 67 Kai Proceedings of the Japanese Cancer Association. Sep. 30, 2008. p. 443. Abstract P-8255.

Takahashi et al., Identification and functional analysis of novel cancer stem cell antigen SMCP. Proceedings of the Japanese Society of Pathology. Mar. 20, 2009;98(1):326.

Torigoe et al., Development of cancer stem cell vaccine. Abstracts for the 25th annual scientific meeting of the international society for biological therapy of cancer. Journal of Immunotherapy. Oct. 1, 2010;33(8):859-920; See pp. 911-912.

Torigoe et al., Clinical trial of survivin2B peptide vaccine: From bed to bench. Japanese Journal of Clinical Immunology. Aug. 31, 2008;31(4):244.

Torigoe et al., Identification of cancer stem cell antigens and development of an immunotherapy. Proceedings of the Japanese Society of Pathology. Mar. 20, 2009;98(1):169.

Zhang et al., Identification and characterization of ovarian cancer-initiating cells from primary human tumors. Cancer Res. Jun. 1, 2008;68(11):4311-20.

Zirlik et al., Cytotoxic T cells generated against heteroclitic peptides kill primary tumor cells independent of the binding affinity of the native tumor antigen peptide. Blood. Dec. 1, 2006;108(12):3865-70. Epub Aug. 10, 2006.

Zou, Cancer initiating cells or cancer stem cells in the gastrointestinal tract and liver. J Cell Physiol. Dec. 2008;217(3):598-604.

EP 09823303.4, Mar. 6, 2012, Extended European Search Report.
PCT/JP2009/005676, Dec. 1, 2009, International Search Report.
PCT/JP2009/005676, Sep. 7, 2010, International Preliminary Report on Patentability.

\* cited by examiner

FIG. 5

Expression of cancer stem cell antigen SOX2 in lung cancer
(immunohistochemical staining)

MOLECULAR MARKER FOR CANCER STEM CELL

RELATED APPLICATIONS

This application is a divisional of U.S. patent application Ser. No. 13/967,410, filed Aug. 15, 2013, now U.S. Pat. No. 9,399,760, which is a divisional of U.S. patent application Ser. No. 13/126,039, filed Jul. 15, 2011, now U.S. Pat. No. 8,541,544, which is a national stage filing under 35 U.S.C. § 371 of International Application PCT/JP2009/005676, filed Oct. 27, 2009, the disclosure of each of which is incorporated by reference herein in their entirety.

TECHNICAL FIELD

The present invention relates to a molecular marker for detecting cancer stem cells in a cell population as a detection target, the molecular marker being detected in cancer stem cells contained in the detection target but not being detected in normal cells or cancer cells other than cancer stem cells.

BACKGROUND ART

It is thought that cancer stem cells are the main cause of recurrence or metastasis of cancer, and the importance of targeting cancer stem cells in cancer therapy has been pointed out. However, the proportion of cancer stem cells in tumor tissue is very low (Non-Patent Document 4), and it is very difficult to specifically recognize and treat cancer stem cells. The development of techniques for detecting cancer stem cells and new therapies targeting cancer stem cells are important issues in cancer care.

Currently, molecular markers such as CD133, CD24, and CD44 are known as a cancer stem cell marker (Non-Patent Documents 1 to 7), but it is said that they are effective only in a few sort of cancer cells, and it is necessary to identify new molecular markers in order to detect cancer stem cells in a greater variety of cancers.

PRIOR ART DOCUMENTS

[Non-Patent Document 1] Shu Zhang et al., Cancer Res. 68: (11) 4311-4320, 2008
[Non-Patent Document 2] Shih-Hwa Chiou et al., Clin. Cancer Res. 14(13) 4085-4095, 2008
[Non-Patent Document 3] Gang-Ming Zou, J. Cell. Physiol. 217: 598-604, 2008
[Non-Patent Document 4] Cheong J. Lee et al., J Clin Oncol 26: 2806-2812, 2008
[Non-Patent Document 5] Madhuri Kakarala et al., J Clin Oncol 26: 2813-2820, 2008
[Non-Patent Document 6] Craig D. Peacock et al., J Clin Oncol 26: 2883-2889, 2008
[Non-Patent Document 7] Xing Fan et al., J Clin Oncol 26: 2821-2827, 2008

SUMMARY OF INVENTION

Problems to be Solved by the Invention

It is an object of the present invention to provide a molecular marker useful for detecting cancer stem cells.

Means for Solving the Problems

While the present inventors have been carrying out an intensive investigation in order to solve the above-mentioned problems, they have noted a new finding that, with regard to at least one tissue, preferably a plurality of tissues in terms of higher usefulness, it is indispensable for a cancer stem cell marker gene not to be expressed in normal cells derived from the tissue but to be expressed in cancer stem cells; that is, to be hardly expressed in normal tissues in a sample, since the sample for identifying a cancer stem cell gene usually contains normal tissue. It has also been discovered that almost all of the cancer stem cell marker genes reported so far are expressed in normal tissue at a high level, and as a result of further investigation by the present inventors it has been found that Sex determining Region Y-box2 (Sox2) gene, which is known as a transcription factor, is not expressed in adult normal cells but is unexpectedly expressed in cancer stem cells. As a result of further investigation, it has been found that other genes, including Sperm Mitochondria-associated Cysteine-rich Protein (Smcp) gene, are hardly expressed in an adult normal cells but are expressed in cancer stem cells, and the present invention has thus been accomplished.

That is, the present invention relates to a molecular marker for detecting cancer stem cells in a cell population as a detection target, wherein the molecular marker being detected in cancer stem cells contained in the detection target but not being detected in normal cells or cancer cells other than cancer stem cells.

Furthermore, the present invention relates to the molecular marker, wherein the detection target is one or more cell- or tissue-derived cell population selected from the group consisting of heart, brain, placenta, lung, liver, skeletal muscle, kidney, pancreas, spleen, thymus, prostate, testis, ovary, small intestine, leucocyte, colon, stomach, bone marrow, large intestine, and peripheral blood mononuclear cells.

Furthermore, the present invention relates to the molecular marker, wherein it is not detected in normal cells or cancer cells other than cancer stem cells for all detection targets.

Moreover, the present invention relates to the molecular marker, wherein the molecular marker is an expression product of one or more genes selected from the group consisting of Or7c1, Dnajb8, Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, and Scgb3a1.

Furthermore, the present invention relates to a method for determining the presence or absence of cancer stem cells in a determination target using the molecular marker as an indicator.

Moreover, the present invention relates to the method, wherein the cell population contains normal cells and/or cancer cells other than cancer stem cells.

Furthermore, the present invention relates to the method, wherein the cell population is derived from one or more cell or tissue selected from the group consisting of heart, brain, placenta, lung, liver, skeletal muscle, kidney, pancreas, spleen, thymus, prostate, testis, ovary, small intestine, leucocyte, colon, stomach, bone marrow, large intestine, and peripheral blood mononuclear cells.

Moreover, the present invention relates to the method, wherein it is determined that cancer stem cells are present when an expression product of one or more genes selected from the group consisting of Or7c1, Dnajb8, Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, and Scgb3a1 is detected.

Furthermore, the present invention relates to the method, wherein the expression product of the gene is mRNA and/or endogenous polypeptide.

Moreover, the present invention relates to the method, wherein the expression product of the gene is mRNA, and the method comprises detecting mRNA by an RT-PCR method.

Furthermore, the present invention relates to the method, wherein the expression product of the gene is endogenous polypeptide, and the method comprises detecting endogenous polypeptide by means of a reagent that specifically reacts with it.

Moreover, the present invention relates to the method, wherein the reagent is an antibody.

Furthermore, the present invention relates to the method, wherein determination is carried out in vitro or in vivo.

Moreover, the present invention relates to a method for screening a cancer therapeutic agent, wherein the method including i) a step of measuring a detected amount "A" of the molecular marker before administering a candidate compound to a cell population,
ii) a step of administering a candidate compound to the cell population,
iii) a step of measuring a detected amount "B" of the molecular marker measured in i) after administering the candidate compound to the cell population, and
iv) a step of determining that a candidate compound is a candidate for a cancer therapeutic agent when A is significantly larger compared to B.

Furthermore, the present invention relates to a kit for determining the presence or absence of cancer stem cells, wherein the kit including a reagent for detecting the molecular marker.

Moreover, the present invention relates to the kit, wherein the reagent for detection is a probe and/or a primer for detecting mRNA that is an expression product of one or more genes selected from the group consisting of Or7c1, Dnajb8, Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, and Scgb3a1, wherein the probe and/or primer comprising a nucleotide sequence complementary to the gene.

Furthermore, the present invention relates to the kit, wherein the reagent for detection is an antibody for detecting a polypeptide that is an expression product of one or more genes selected from the group consisting of Or7c1, Dnajb8, Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, and Scgb3a1.

Moreover, the present invention relates to a method for determining a cancer employing the kit.

Furthermore, the present invention relates to a polypeptide that can be used as an antigen for inhibiting the function of cancer stem cells or killing cancer stem cells, wherein the polypeptide being a polypeptide coded by Or7c1, Dnajb8, Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, or Scgb3a1, or a portion thereof, or a polypeptide in which one or several amino acids in the polypeptide or a portion thereof are deleted, substituted, or added.

Moreover, the present invention relates to an antibody that specifically reacts with an epitope derived from an expression product of one or more genes selected from the group consisting of Or7c1, Dnajb8, Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, and Scgb3a1.

Furthermore, the present invention relates to a pharmaceutical composition that comprises at least one of the polypeptide and/or the antibody.

Moreover, the present invention relates to the pharmaceutical composition, wherein the pharmaceutical composition is used for treating or preventing cancer.

Furthermore, the present invention relates to a method for inhibiting the function of cancer stem cells or killing cancer stem cells by using the polypeptide as an antigen.

Moreover, the present invention relates to the method, wherein the method employs the antibody.

Furthermore, the present invention relates to a nucleic acid encoding the polypeptide.

Moreover, the present invention relates to a pharmaceutical composition that comprises the nucleic acid.

Furthermore, the present invention relates to the pharmaceutical composition, wherein the pharmaceutical composition is for a DNA or RNA vaccine.

Moreover, the present invention relates to a method for screening a peptide that is presented on a major histocompatibility complex as an antigen, wherein the method including i) a step of preparing a peptide having an appropriate length into which a target polypeptide is fragmented,
ii) a step of culturing together the fragmented peptide obtained in i), antigen presenting cells, and T cells sensitized against the target polypeptide and/or the fragmented peptide obtained in i),
iii) a step of measuring the level of activation of the T cells obtained in ii), and
iv) a step of selecting a fragmented peptide that has activated T cells in iii), and the target polypeptide being the polypeptide above.

Furthermore, the present invention relates to a nucleic acid used for suppressing the expression of a gene in cancer stem cells selected from the group consisting of Or7c1, Dnajb8, Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, and Scgb3a1.

Moreover, the present invention relates to the nucleic acid, wherein the nucleic acid is DNA and/or RNA.

Furthermore, the present invention relates to a pharmaceutical composition that comprises at least one of the nucleic acid.

Moreover, the present invention relates to the pharmaceutical composition, wherein the pharmaceutical composition is for treating cancer.

Furthermore, the present invention relates to a method for inhibiting the function of cancer stem cells by using the nucleic acid.

Effects of the Invention

The molecular marker provided by the present invention can discriminate between cancer stem cells contained in cancer cells and cancer cells other than cancer stem cells. Furthermore, since the discrimination may be carried out by detection of a single molecular marker, cancer stem cells can be discriminated very easily.

Moreover, since the molecular marker of the present invention may be used in common for a plurality of cancer stem cells such as lung cancer cells, breast cancer cells, and colorectal cancer cells, it is very effective as a versatile molecular marker for cancer stem cells.

Furthermore, since the molecular marker of the present invention is not detected at all or is hardly detected in normal cells, it is useful for the discrimination of cancer stem cells and, moreover, for the discrimination of tumor tissue containing cancer stem cells.

Moreover, the molecular marker of the present invention has high relevance to tumorigenicity and is useful in cancer stem cell immunotherapy, molecular targeted therapy or gene transfer therapy targeted thereat, as well as the screening of drugs, peptides, etc. that can be used in cancer therapy.

BRIEF DESCRIPTION OF DRAWINGS

FIG. 5 is a diagram showing a chart of expression in each of the cells for the genes that were examined. In the diagram, ones where expression was not seen are given as negative, ones where expression was seen are given as positive, and ones where, although there was very slight expression, it was a trace amount of expression that could not be said to be significant expression are given as false positive. Ones that are false positive are determined to be 'not detected'. In the diagram, LHK2 is lung cancer, MFH03 is soft tissue sarcoma, MCF7 is breast cancer, LHK2-SOX2 is LHK2 cell line with SOX2 gene overexpressed, and SW480 and KM12 are large colorectal cancer cell lines.

BEST MODE FOR CARRYING OUT THE INVENTION

Figure 1:
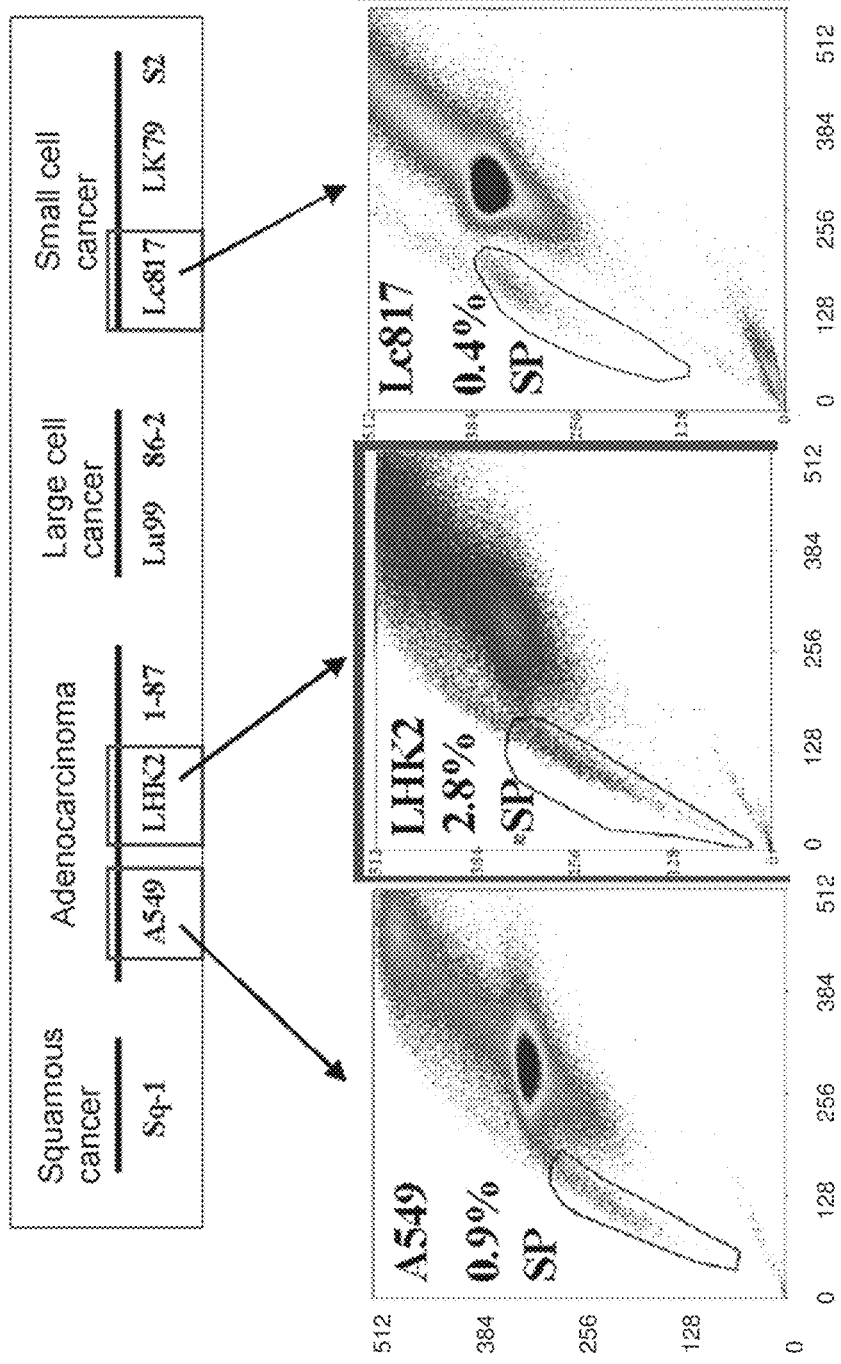
FIG. 1 is a diagram showing the result of SP analysis of lung cancer cell lines. Parts surrounded by a line correspond to the respective SP fractions, and % denotes the proportion of SP fraction cells in the total cells.

The present invention is explained in detail below.

The molecular marker of the present invention is a molecular marker for detecting cancer stem cells in a cell population as a detection target, the molecular marker being detected in cancer stem cells contained in the detection target but not being detected in normal cells or cancer cells other than cancer stem cells. Therefore, it is typically used for detecting cancer stem cells from a cancer cell population. Furthermore, for example, when collecting an arbitrary cell population as a detection target, normal cells are sometimes mixed in and it becomes a cell population in which cancer stem cells, cancer cells other than cancer stem cells, and normal cells are mixed, and even in such a case cancer stem cells can be detected correctly.

The 'cancer stem cells' referred to in the present invention are cells that, among cancer cells, have properties as stem cells. Stem cells are cells that maintain the potential for differentiation after cell division. When cancer stem cells are stained with a Hoechst fluorescent dye (Hoechst33342) and subjected to detection by flow cytometry using a UV laser (wavelength about 350 nm) as excitation light, they are concentrated in a Side Population (SP) fraction. The SP fraction referred to here indicates a fraction that is not stained by the Hoechst fluorescent dye, as a result of the dye being eliminated from the cell via an ABC transporter, etc, in contrast to a Main Population (MP) fraction that is stained by the dye.

The 'normal cells' referred to in the present invention mean cells that have normal function in the activity of a living body or tissue. The normal cells may contain somatic stem cells but are preferably mature cells.

The molecular marker of the present invention is preferably detected in common in cancer stem cells of a plurality of types of cancer, and may be used as a single marker in a plurality of types of cancer. It is expressed in common in cancer stem cells of a plurality of types of cancer derived from cells or tissue of, for example, heart, brain, placenta, lung, liver, skeletal muscle, kidney, pancreas, spleen, thymus, prostate, testis, ovary, small intestine, leucocyte, colon, stomach, bone marrow, large intestine, peripheral blood mononuclear cells, etc., and can therefore be detected.

Furthermore, the molecular marker of the present invention is not detected in cancer cells other than cancer stem cells or in normal cells. Preferably, it is not detected in cancer cells other than cancer stem cells or in normal cells in at least one of, for example, heart, brain, placenta, lung, liver, skeletal muscle, kidney, pancreas, spleen, thymus, prostate, testis, ovary, small intestine, leucocyte, colon, stomach, bone marrow, large intestine, and peripheral blood mononuclear cells.

The molecular marker of the present invention can be expressed or detected in cancer stem cells but cannot be expressed or detected in normal cells, and it is therefore possible to detect cancer stem cells in a cell population arbitrarily collected from cells or tissue containing cancer stem cells.

In order to use it as a versatile molecular marker, it is preferable for it to be used as a single marker in a plurality of types of cancer, and it is typically not detected in normal cells of at least two types of cells or tissue of heart, brain, placenta, lung, liver, skeletal muscle, kidney, pancreas, spleen, thymus, prostate, testis, ovary, small intestine, leucocyte, colon, stomach, bone marrow, large intestine, peripheral blood mononuclear cells, etc., and it is preferably not detected in at least three thereof. It is most preferably not detected in normal cells of all types of cells or tissue.

The 'gene expression' referred to in the present specification means a series of biological reactions with gene transcription as a starting point, and the 'expression product' means a molecule such as, for example, mRNA or endogenous polypeptide, generated by this series of biological reactions.

Furthermore, 'being expressed' referred to in the present specification means that an expression product can be identified by a method known to a person skilled in the art, such as for example RT-PCR, in-situ hybridization, immunoassay, or a chromatographic method. Moreover, 'not being detected' means that no expression product is identified by the above-mentioned methods for identifying an expression product. In addition, even if there is a signal detected by a detection method having very high sensitivity such as for example RT-PCR, when there is a large difference in signal intensities, or when it is below the detection level in a detection method such as an immunoassay having sufficient sensitivity from the viewpoint of practicality in the embodiment of the present invention, it is included in the 'not being detected' defined in the present specification.

An expression product of a gene detected by the present invention is preferably an expression product of a gene having a known sequence, but may be a homologue thereof. It is preferably an expression product of a gene having an mRNA or cDNA sequence below.

Sox2: Gene accession No. NM 003106
Smcp: Gene accession No. NM_030663
Ints1: Gene accession No. NM_001080453
Kox12: Gene accession No. NM_152907
Mdf1: Gene accession No. NM_005586
FLJ13464: Gene accession No. AK023526
667J232: Gene accession No. AL833225
Surf6: Gene accession No. NM_006753
Pcdh19: Gene accession No. NM_001105243
Dchs2: Gene accession No. NM_017639
Pcdh21: Gene accession No. NM_033100
Gal3st1: Gene accession No. NM_004861
Rasl11b: Gene accession No. NM_023940
Hes6: Gene accession No. NM_018645
Znf415: Gene accession No. NM_018355
Nkx2-5: Gene accession No. NM_004387
Pamci: Gene accession No. NM_005447
Pnmt: Gene accession No. NM_002686
Scgb3a1: Gene accession No. NM_052863
Or7c1: Gene accession No. NM_198944
Dnajb8: Gene accession No. NM_153330

The determination target in the present invention is preferably a human, human-derived tissue, and/or human-derived cells, but may be an animal other than a human (e.g. rodents such as mouse, rat, guinea pig, or hamster, primates such as chimpanzee, artiodactyla such as cattle, goat, or sheep, perissodactyla such as horse, rabbit, dog, cat, etc.), said animal-derived tissue, and/or said animal-derived cells.

With regard to the determination, when the molecular marker of the present invention is detected, it is determined that there are cancer stem cells, and the determination target may contain normal cells and/or cancer cells other than cancer stem cells. From the viewpoint of the capability of being utilized as a single marker in a plurality of types of cancer, determination is carried out by detecting preferably expression products of Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, Scgb3a1, Or7c1, and Dnajb8, and most preferably an expression product of Sox2.

When the molecular marker of the present invention is mRNA, a reagent that specifically binds to mRNA such as a probe or a primer is used for the detection thereof. From the viewpoint of the level of detection sensitivity or simplicity of operation, it is detected by an RT-PCR method.

When the molecular marker of the present invention is an endogenous polypeptide, a reagent that specifically binds to a peptide such as an antibody or a ligand is used for the detection thereof. For example, with regard to an antibody, a polyclonal antibody and/or a monoclonal antibody may be used. From the viewpoint of a non-specific reaction being lower, it is preferable to use a monoclonal antibody.

Determination may be carried out in vivo or in vitro. 'Determination in vitro' referred to in the present specification means determination being carried out after tissue or cell collected from a living body is grown in an environment outside a living body, such as for example a culture liquid. In contrast thereto, 'determination in vivo' means determination being carried out directly within a living body or, after collecting tissue or cell from a living body, determination being carried out immediately or after immobilization. Collecting of tissue or cell is carried out by, but is not limited to, for example incision, cell suction, blood collection, urine collection, etc.

When determination is carried out in vivo, an in vivo detection method known to a person skilled in the art may be employed. Determination in vivo may be carried out by a known detection method such as a blood test, in situ hybridization, in situ PCR, or immunohistochemical staining.

When determination is carried out in vitro, it may be carried out by, but is not limited to, for example an in vitro detection method known to a person skilled in the art such as immunohistochemical staining or RT-PCR. When RT-PCR is carried out, the number of cycles is preferably 30 to 35 cycles. Determination in tumor tissue after tissue culturing is also included in determination in vitro.

Since the molecular marker of the present invention is specifically expressed in cancer stem cells, the amount detected is expected to have a correlation with the number of cancer stem cells. Therefore, before and after administering a candidate compound to a target, if the amount of the molecular marker of the present invention detected has decreased, it can be expected that the number of cancer stem cells will have decreased. That is, by comparing the amount of molecular marker detected before administration and that after, it is possible to screen compounds that are candidates for a therapeutic agent for cancer stem cells. Therefore, such a screening method is also included in the present invention.

Furthermore, the present invention includes a kit containing a reagent for detecting the molecular marker. The kit contains, for example, in order to detect mRNA, a reagent that specifically detects mRNA, such as a probe or a primer and, in order to detect polypeptide, a reagent that specifically detects polypeptide, such as a ligand or an antibody. The kit contains at least one of the above-mentioned reagents. The kit may contain an accompanying reagent suitable for the form of the application, such as for example a reaction buffer or a reaction promoter.

From the viewpoint of a single kit being utilized in a plurality of types of cancer, it preferably contains a reagent that detects a gene product of the gene sequence Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, Scgb3a1, Or7c1, or Dnajb8, and most preferably Sox2.

The 'probe and/or primer having a complementary nucleotide sequence to a gene' referred to in the present invention is DNA or RNA having a complementary sequence so as to specifically bind to a partial sequence of the gene sequence, and may be optionally labeled with for example a fluorescent label or a radioisotope label.

A method for determining whether or not a determination target is a cancer by detecting cancer stem cells using the above-mentioned kit is also included in the present invention.

A polypeptide that functions as the molecular marker of the present invention can be used as an antigen for inhibiting the function of cancer stem cells or killing them. These polypeptides may have a functional site such as for example an antibody recognition site or a protein binding site, which may have a length of for example 9 to 11 amino acids. In a case in which a functional site appears after some modification or transformation, such as for example a case in which a protein three-dimensional structure is recognized by an antibody, a case in which a multimer is recognized by an antibody, or a case in which an antibody recognition site is formed by binding of a modifying group, the polypeptides may also have this functional site structure. These polypeptides are preferably derived from expression products of genes selected from the group consisting of Sox2, Smcp, Ints1, Kox12, Mdf1, FLJ13464, 667J232, Surf6, Pcdh19, Dchs2, Pcdh21, Gal3st1, Rasl11b, Hes6, Znf415, Nkx2-5, Pamci, Pnmt, Scgb3a1, Or7c1, and Dnajb8.

Examples of the method for killing cancer stem cells using these polypeptides as an antigen include, but are not limited to, a method involving CTL induction, a method in which an immunoreaction utilizing a polypeptide-specific antibody is caused, and a method in which function is inhibited or antagonized by binding to a polypeptide.

When an epitope derived from an expression product of the gene of the present invention binds to an antibody that specifically reacts therewith, the bound antibody becomes a signal to thus activate an immunoreaction. Since the epitope is itself a molecular marker or a partial structure thereof that is specifically expressed in cancer stem cells, this strongly suggests that binding of a specific antibody enables an immune cascade that specifically recognizes cancer stem cells to be activated. Furthermore, it is also possible to use an antibody conjugated with a drug that attacks cancer cells etc. They enable application to the so-called missile therapy in which cancer stem cells are targeted.

Therefore, an antibody used in the above-mentioned method and a pharmaceutical composition containing a polypeptide and/or an antibody are also included in the present invention.

Examples of the pharmaceutical composition include, but are not limited to, a cancer vaccine and an anticancer agent. These compositions may contain, in addition to the polypeptide and/or antibody of the present invention, for example, a drug having antitumor activity, an adjuvant, a pharmaceutically acceptable carrier, etc. as necessary.

Moreover, a nucleic acid coding for the above-mentioned polypeptide and a pharmaceutical composition containing the nucleic acid are also included in the present invention. Examples of the pharmaceutical composition containing the nucleic acid include, but are not limited to, a DNA vaccine. These compositions may contain, in addition to the nucleic acid of the present invention, for example, a drug having antitumor activity, an adjuvant, a pharmaceutically acceptable carrier, etc. as necessary.

Among polypeptide fragments that are the molecular marker of the present invention, there are those that are antigen-presented by a protein called a major histocompatibility complex (MHC molecule). Cytotoxic T cells (CTLs) recognize a specific antigen bound to an MHC class I molecule and cause an immunoreaction that induces apoptosis of antigen presenting cells.

As a result of research by the present inventors, it has been found that, among polypeptides derived from the molecular marker of the present invention, a portion of polypeptides exhibit a high affinity for HLA-A24, which is one of the human MHC molecules, and it has further been found that some of them have the capability of inducing CTLs and leading cells to apoptosis. This result strongly suggests that the polypeptide of the present invention can give immunological memory with respect to cancer stem cells. This substantially shows that the polypeptide of the present invention can be applied to a method for specifically treating cancer stem cells.

It is suggested that, since the molecular marker of the present invention is specifically expressed in cancer stem cells, some part of the polypeptide is antigen-presented via MHC molecules. Screening of polypeptides (epitope peptides) that are antigen-presented via MHC molecules is useful in the treatment of cancer. Therefore, such a screening method is also included in the present invention.

Screening may employ a normal epitope mapping method. For example, after a plurality of types of fragmented peptide having an appropriate length are prepared from a target polypeptide, the target polypeptide and/or the fragmented peptide, antigen presenting cells, and T cells are cultured together to thus sensitize the T cells. The sensitized T cells, antigen presenting cells, and fragmented peptide are then cultured together, thus restimulating the T cells. The degree of activation of the T cells is then measured, peptides having a high degree of activation are selected, and an epitope sequence is determined. In this case, the degree of activation may be determined as appropriate by a method known to a person skilled in the art such as measurement of cytotoxic activity or amount of cytokine produced. Furthermore, by specifying the HLA type of the T cells, an antigen peptide that is restricted by the specific HLA type is selected.

DNA that functions as the molecular marker of the present invention is DNA that is specifically expressed in cancer stem cells, and it is thought that by suppressing the expression thereof the function of cancer stem cells can be suppressed. Therefore, a nucleic acid for suppressing the expression of DNA that functions as the molecular marker of the present invention is also included in the present invention.

Examples of the method for suppressing expression include, but are not limited to, RNAi or expression of a repressor. Therefore, examples of nucleic acids for suppressing the expression of DNA include, but are not limited to, siRNA, shRNA, and shDNA. The nucleic acid may have any length as long as there is a sufficient number of bases in order to suppress the expression of DNA.

Other than DNA and RNA, the nucleic acid may be a nucleic acid analog, but from the viewpoint of versatility is preferably DNA and/or RNA.

It is suggested that there is a possibility of cancer stem cells being specifically and/or efficiently attacked by suppressing the expression of DNA that functions as the molecular marker of the present invention. That is, it is suggested that the above-mentioned nucleic acid may be applied to gene transfer therapy. Therefore, a pharmaceutical composition containing the nucleic acid of the present invention is also included in the present invention.

The above-mentioned pharmaceutical composition may be used as, for example, a cancer therapeutic agent such as an anticancer agent, a metastasis inhibitor, or a cancer vaccine such as a DNA vaccine, but is not limited thereto. These pharmaceutical compositions may contain, in addition to the nucleic acid of the present invention, for example, a drug having antitumor activity, an adjuvant, a pharmaceutically acceptable carrier, etc. as necessary.

Furthermore, a method of suppressing expression of DNA that functions as the molecular marker of the present invention in cancer stem cells using the nucleic acid of the present invention is also included in the present invention.

Experimental examples below are for explaining the present invention more specifically, but do not limit the scope of the present invention. A person skilled in the art having usual knowledge and skill can modify in a variety of ways embodiments shown in the Experimental Examples below as long as the modifications do not depart from the spirit of the present invention, and such modified embodiments are also included in the present invention.

EXAMPLE 1

Experimental Example 1

Isolation of Cancer Cell SP Fraction a) Preparation of Reagent

A 5% anti-fetal bovine serum (FCS)-containing DMEM medium was prepared, and warmed to 37° C. 50 mM Verapamil was prepared, and diluted to 5 mM with 5% FCS+DMEM. Hoechst 33342 was adjusted to 250 µg/mL with 5% FCS+DMEM. DNaseI was adjusted to 1 mg/mL with DDW, and subjected to filtration sterilization using a 0.2 µm filter.

b) Preparation of Cells for Flow Cytometry (FACS)

Cells were suspended in 4 mL of 5% FCS+DMEM, and the number of cells was counted. Furthermore, the cell concentration was adjusted to $1 \times 10^6$ counts/mL by adding 5% FCS+DMEM, and 1 mL was sampled in a Falcon tube for verapamil (+). The verapamil (+) cells and the remaining cells (for verapamil (−)) were incubated in a water bath at 37° C. for 10 minutes. After incubation, a verapamil solution was added to the verapamil (+) such that the final concentration of verapamil became 50 to 75 µM, and a Hoechst 33342 solution was then added to the verapamil (+) and the verapamil (−) such that the final concentration of Hoechst 33342 became 2.5 µM to 5.0 µM.

The cells were incubated at 37° C. for 90 minutes with shaking, immediately followed by cooling on ice. Centrifugation was carried out at 1100 to 1500 rpm at 4° C. for 3 minutes, and supernatant was removed. The cells were suspended with 1×PBS+5% FCS, and the suspension was transferred to an ice-cooled FACS tube. Centrifugation was carried out again at 1100 to 1500 rpm at 4° C. for 3 minutes, supernatant was removed, and the cells were suspended with 1×PBS+5% FCS. Centrifugation was carried out once again at 1100 to 1500 rpm at 4° C. for 3 minutes, supernatant was removed, and the cells were suspended with 500 µL of 1×PBS+5% FCS to which EDTA was added at a final concentration of 2 mM. 0.5 µL of DNAseI solution was added, pipetting was carried out, and it was passed through a filter for FACS. 0.5 µL of 1 mg/mL propidium iodide (PI) was added, and FACS was carried out at a flow rate of 1000 to 2000 counts/sec.

c) Flow Cytometry (FACS)

The flow cytometer used was a BD FACS Aria II special edition (registered trademark) (Becton, Dickinson and Company). FACS operation was carried out in accordance with the instruction manual. First, it was confirmed whether or not SP fraction cells could be detected by passing cells of verapamil (−); after confirmation, verapamil (+) cells were passed while gating the SP fraction, thus confirming whether or not SP fraction cells disappeared. If they disappeared, it was determined that the cells of the fraction were SP fraction cells, and then the cells of the fraction were isolated. The isolated cells were subjected to centrifugation at 4° C. and 1500 rpm for 15 minutes, removing supernatant, and suspended with 100 to 200 µL of 1×PBS, and the number of cells was counted.

From the results, SP fraction cells were detected in adenocarcinoma A549 and LHK2 and small cell cancer Lc817. The results are shown in FIG. 1.

Discussion

Detection of SP fraction cells in adenocarcinoma and small cell cancer, which are of a type in which metastasis easily occurs among lung cancers, coincides with the finding that cancer stem cells are the main cause of metastasis.

EXAMPLE 2

Experimental Example 2

Tumorigenicity Experiment

Figure 2:
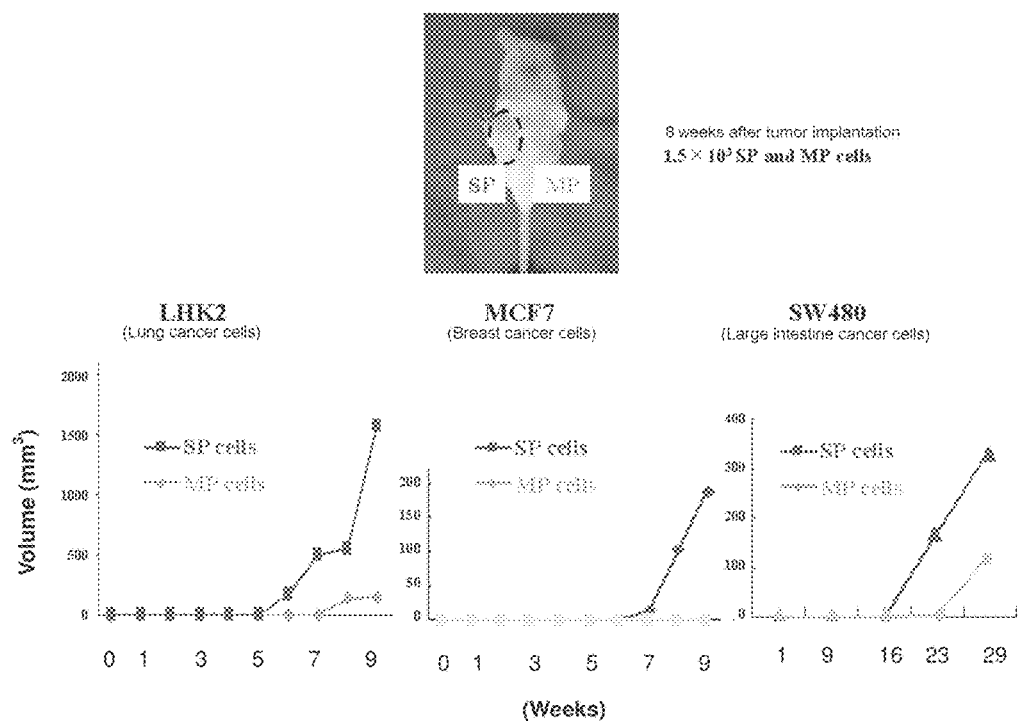
FIG. 2 is a diagram showing the result of a tumorigenicity experiment in NOD/SCID mice. The top panel shows a photograph of a mouse 8 weeks after implantation. The bottom panel shows graphs of the average value for tumor size every week for the groups implanted with 1500 cells of LHK2 (lung cancer cells), MCF7 (breast cancer cells), and SW480 (colorectal cancer cells).

Tumorigenicity was confirmed by inoculating mice with fractioned SP cells and MP cells using each of LHK2, MCF7, and SW480 cell lines by the same method as in Experimental Example 1. The same number of SP cells and MP cells were suspended in 100 µL of 1×PBS on ice and mixed with 100 µL of Matrigel. NOD/SCID mice (obtained from Oriental Kobo Co., Ltd.) were inoculated subcutaneously to the dorsal skin with 100 µL of a cell-Matrigel mixed liquid at 1500 cells per site of each of SP and MP cells; when a tumor started to form, the lengths of the longest diameter and the shortest diameter were measured, and the volume was calculated as approximated to a spheroid and compared. The results are shown in FIG. 2.

From the results, it was found that, compared with MP cells, which did not form a tumor in even one mouse when implanted with 150 cells, the fractioned SP cells from LHK2 had much higher tumorigenicity such that 2 out of 5 mice formed a tumor when implanted with only 15 cells and all 5 mice formed a tumor when implanted with 150 cells. This coincided with the finding that cancer stem cells are the main factor in tumor formation, and cancer stem cells are concentrated in SP fraction cells. (reference Kondo T, Setoguchi T, Taga T. Persistence of a small subpopulation of cancer stem-like cells in the C6 glioma cell line. Proc Natl Acad Sci USA. 20: 781-786, 2004.)

EXAMPLE 3

Experimental Example 3

Confirmation of Expression by DNA Microarray a) Extraction of mRNA

SP cells and MP cells isolated by the same method as in Experimental Example 1 were centrifuged at room temperature at 1500 rpm for 5 minutes, and supernatant was removed. Extraction of mRNA was carried out using an RNeasy Kit (Qiagen) in accordance with the kit protocol.

b) Amplification and Labeling of mRNA

The extracted mRNA was subjected to mRNA amplification using an RNA amplification kit obtained from Sigma Genosys, and the amplified mRNA was subjected to labeling using an mRNA labeling kit obtained from Sigma Genosys so that material extracted from the SP fraction was labeled with Cy5 and material extracted from the MP fraction was labeled with Cy3, and the dyes were exchanged, and that extracted from the SP fraction was labeled with Cy3 and that extracted from the MP fraction was labeled with Cy5.

c) Microarray

SP fraction-derived mRNA and MP fraction-derived mRNA, which had been labeled with different dyes, were mixed, and analyzed for expression of mRNA using a DNA chip (Panorama (registered trademark) Micro Array, Human) obtained from Sigma Genosys hybridized in accordance with the microarray kit protocol. From the results, it was confirmed that Sox2 gene, Smcp gene, Ints1 gene, Kox12 gene, Mdf1 gene, FLJ13464 gene, 667J232 gene, Surf6 gene, Pcdh19 gene, Dchs2 gene, Pcdh21 gene, Gal3st1 gene, Rasl11b gene, Hes6 gene, Znf415 gene, Nkx2-5 gene, Pamci gene, Pnmt gene, Scgb3a1 gene, Or7c1 gene, and Dnajb8 were expressed in the SP fraction but were not expressed in the MP fraction or at a negligible level if expressed.

EXAMPLE 4

Experimental Example 4

Expression of Sox2 a) Primer Used in RT-PCR

A list of primers used in RT-PCR in the Experimental Examples is shown in Table 1.

TABLE 1

| | Forward primer | Reverse primer |
|---|---|---|
| Sox2 | acttttgtcggagacggaga (SEQ ID NO: 1) | gttcatgtgcgcgtaactgt (SEQ ID NO: 2) |
| Smcp | tgtgtgaccagacaaaacacag (SEQ ID NO: 3) | gttgggctcagactccatgt (SEQ ID NO: 4) |
| Ints1 | tgtccagcatgagcaaactc (SEQ ID NO: 5) | aaaccgtagcagggtcacac (SEQ ID NO: 6) |
| Kox12 (Znf19) | atgtggaaaagcaccaggac (SEQ ID NO: 7) | tcctctggtgccgaattaac (SEQ ID NO: 8) |
| Mdf1 | caggaagactgctgtgtcca (SEQ ID NO: 9) | atgcagatctccaggcagtc (SEQ ID NO: 10) |
| FLJ13464 | tgcataacaccaaaggtcca (SEQ ID NO: 11) | gacctggccaatacaatgct (SEQ ID NO: 12) |
| 667J232 | aggacatgcctgggtgatag (SEQ ID NO: 13) | cccaatcctgagttcttcca (SEQ ID NO: 14) |
| Surf6 | cgactgcatgagaagatcca (SEQ ID NO: 15) | gaggaggttggtccacttca (SEQ ID NO: 16) |
| Pcdh19 | cccaaggtcaacagcgttat (SEQ ID NO: 17) | cacaccaggggactctttgt (SEQ ID NO: 18) |
| Dchs2 | gaaggagatcaagggaagg (SEQ ID NO: 19) | atcaaaggggtggaaaaac (SEQ ID NO: 20) |
| Pcdh21 | atgcagaggaacccaacaac (SEQ ID NO: 21) | tgagtaaggctgtggtgctg (SEQ ID NO: 22) |
| Gal3st1 | ggcctgcttcaacatcatct (SEQ ID NO: 23) | gctgttgtcatagcccaggt (SEQ ID NO: 24) |
| Rasl11b | tgtggtgatcgttttctcca (SEQ ID NO: 25) | agggaggttcttcgcttctc (SEQ ID NO: 26) |
| Hes6 | agctcctgaaccatctgctc (SEQ ID NO: 27) | agcaggagcctgactcagtt (SEQ ID NO: 28) |
| Znf415 | cttgcaaggcattggagaat (SEQ ID NO: 29) | taggcttgaatgcacactga (SEQ ID NO: 30) |
| Nkx2-5 | acgcccttctcagtcaaaga (SEQ ID NO: 31) | ttttcggctctagggtcctt (SEQ ID NO: 32) |
| Pamci (Rassf9) | tgatcatttcccaggaccat (SEQ ID NO: 33) | cccttccgcatcttcattta (SEQ ID NO: 34) |
| Pnmt | gaatgctggcaggataagga (SEQ ID NO: 35) | cttgtagccactacgcacca (SEQ ID NO: 36) |
| Scgb3a1 | ctccgctgctgctttcttag (SEQ ID NO: 37) | ccagctcagccacactt (SEQ ID NO: 38) |

TABLE 1-continued

|  | Forward primer | Reverse primer |
|---|---|---|
| Or7c1 (Tpcr86) | agctctgtggactgc tggtt (SEQ ID NO: 39) | ggacgccagttgcaa agtat (SEQ ID NO: 40) |
| Dnajb8 | ccgacaagaaccctg acaat (SEQ ID NO: 41) | aggtggatgagaagg tggtg (SEQ ID NO: 42) |
| G3PDH | accacagtccatgcc atcac (SEQ ID NO: 66) | tccaccaccctgttg ctgta (SEQ ID NO: 67) | b) Expression of Sox2 in Normal Cells

In order to further confirm the usefulness of Sox2, which had been confirmed in Experimental Example 3c), expression thereof was examined in human adult normal cells. RT-PCR was carried out using a human adult normal tissue-derived mRNA panel obtained from Clontech. The mRNA panel includes mRNA derived from adult normal cell and tissue of each of heart, brain, placenta, lung, liver, skeletal muscle, kidney, pancreas, spleen, thymus, prostate, testis, ovary, small intestine, large intestine, and peripheral blood mononuclear cells.

First, cDNA was synthesized from mRNA using a SuperScript (registered trademark) III reverse transcription enzyme (Invitrogen) in accordance with the kit protocol.

The cDNA thus synthesized was subjected to Sox2 cDNA amplification by RT-PCR using forward primer and reverse primer (see Table 1). As a control, G3PDH cDNA was amplified by the same method. PCR conditions are shown in Table 2.

TABLE 2

| 94° C. | 2 min | — |
|---|---|---|
| 94° C. | 15 sec | 30 to 35 cycles |
| 58° C. to 60° C. | 30 sec | |
| 72° C. | 30 sec | |
| 72° C. | 2 min | — |

The amplification product thus amplified was subjected to electrophoresis at 100 V for 25 minutes using 1.5% agarose gel. The results are shown in FIG. 3a).

c) Expression of Sox2 in Cancer Cell Line

Figure 3:
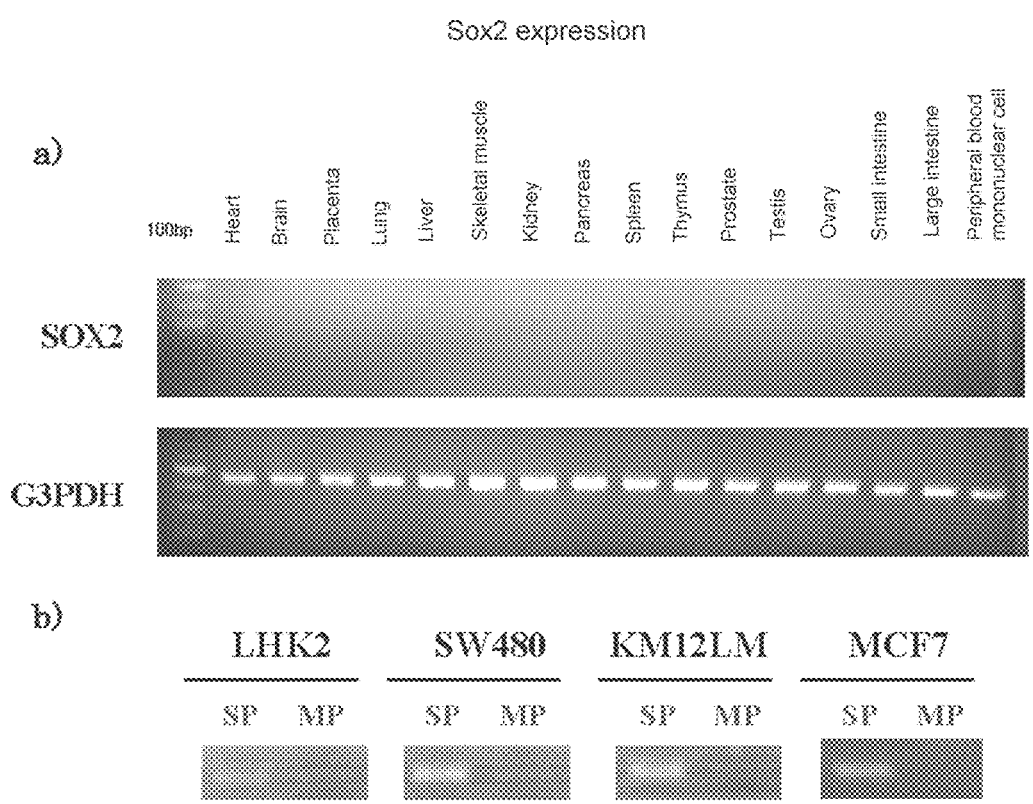
FIG. 3 is a diagram showing expression of Sox2 in a) human adult normal cells and b) in the SP fraction and MP fraction of cancer cell lines.

Lung cancer cell line LHK2, colorectal cancer cell lines SW480 and KM12LM, and breast cancer cell line MCF7 were separated into SP fraction and MP fraction in the same way as in Experimental Example 1. mRNA was extracted from the SP fraction and the MP fraction of the above in the same way as in Experimental Example 3a), and cDNA was synthesized in the same way as in Experimental Example 4b). Sox2 cDNA was amplified using a Sox2 primer (see Table 1) under the conditions of Table 2, and the amplification product was subjected to electrophoresis at 100 V for 25 minutes using 1.5% agarose gel. The results are shown in FIG. 3 b).

Discussion

Expression of Sox2 was not observed in human adult normal tissue. This suggests that Sox2 is a marker that does not recognize normal cells in the tissue, and also suggests the possibility of specifically treating tumor cells by the use of Sox2. As a result of examining cells of the SP and MP fractions of the 4 lines LHK2, SW480, KM12LM, and MCF7, strong expression was observed in the SP fraction cells for all lines but there was hardly any expression in the MP fraction cells, suggesting the possibility of using Sox2 as a marker that is specific to SP fraction cells, that is, cancer stem cells.

EXAMPLE 5

Experimental Example 5

Expression of Smcp and FLJ13464

Figure 4:
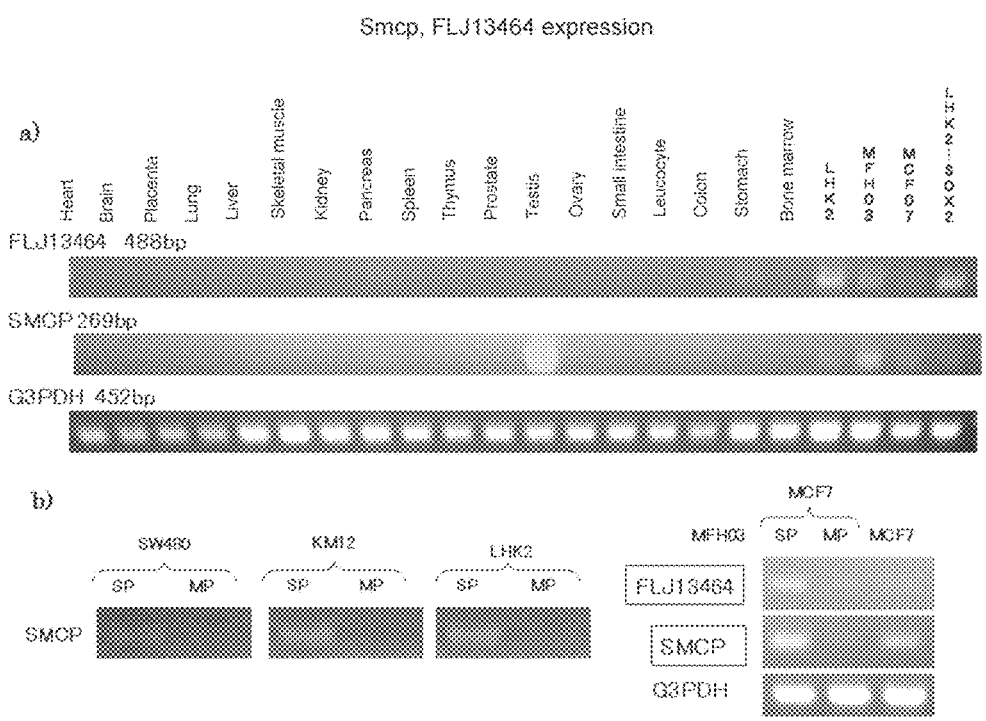
FIG. 4 is a diagram showing expression of Smcp and FLJ13464 in a) human adult normal cells and b) in the SP fraction and MP fraction of cancer cell lines.

In order to further confirm the usefulness of Smcp and FLJ13464, which were confirmed in Experimental Example 3c), the expression thereof in human adult normal tissue and other cancer cells was examined. The human adult normal tissues employed in this experiment were derived from a human adult normal tissue mRNA panel obtained from Clontech containing heart, brain, placenta, lung, liver, skeletal muscle, kidney, pancreas, spleen, thymus, prostate, testis, ovary, small intestine, leucocyte, colon, stomach, and bone marrow, and the cancer cells employed were lung cancer cell line LHK2, large colorectal cancer cell lines SW480 and KM12LM, breast cancer cell line MCF7, and malignant fibrous histiocytoma cell line MFH03.

cDNA was synthesized from mRNA of each cell and tissue in the same way as in Experimental Example 4b). The cDNA thus synthesized was subjected to Smcp and FLJ13464 cDNA amplification using Smcp forward primer and reverse primer (See Table 1) and FLJ13464 forward primer and reverse primer (See Table 1) under the PCR conditions shown in Table 2. As a control, cDNA of G3PDH was amplified by the same method as above. The amplification products thus amplified were subjected to electrophoresis at 100 V for 25 minutes using 1.5% agarose gel. The results are shown in FIG. 4 a).

In the same way as in Experimental Example 4, cDNA was synthesized from SP and MP fraction cells of SW480, KM12, LHK2, and MCF7, cDNA was amplified using a Smcp and FLJ13464 amplification primer set, and the amplification products were subjected to agarose electrophoresis. The results are shown in FIG. 4b).

Discussion

Smcp and FLJ13464 expression was not observed in almost all human adult normal tissue; FLJ13464 was expressed in the pancreas and stomach and Smcp was expressed in the testis to some degree. This suggests that for almost all tissue Smcp and FLJ13464 are markers that do not recognize normal cells in tissue, suggesting the possibility of a tumor cell-specific treatment in tissue where expression is not observed in normal cells. Furthermore, in the same manner as for the results of Experimental Example 4, since Smcp was specifically expressed in the SP fraction cells of SW480, KM12, LHK2, and MCF7, and FLJ13464 was specifically expressed in the SP fraction cells of MCF7, the results show the possibility of Smcp and FLJ13464 being used as cancer cell-specific markers.

EXAMPLE 6

Experimental Example 6

Expression of Other Genes

Figure 5:
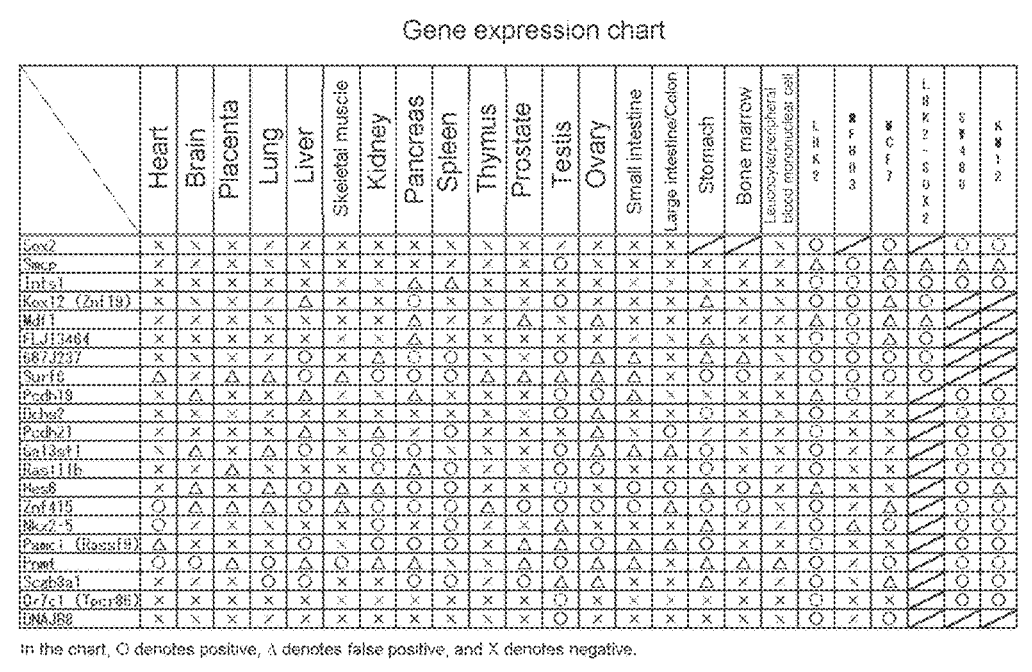

Expression of other genes in normal cells was confirmed in the same way as in Experimental Example 5. The results are shown in FIG. 5 as a chart.

EXAMPLE 7

Experimental Example 7

Expression of Sox2 in Other Cancer Cell Lines

Figure 6:
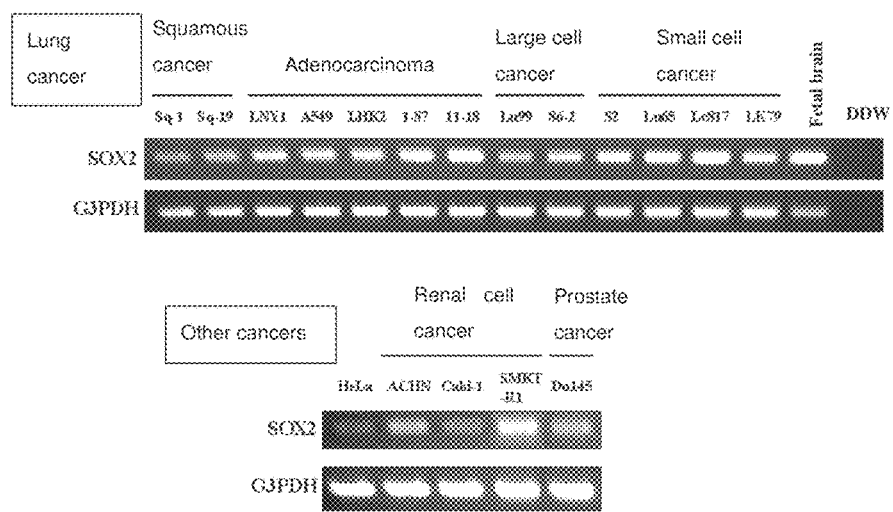
FIG. 6 is a diagram showing expression of Sox2 in other cancer cell lines.

In order to examine in detail whether or not Sox2 is expressed in cancer cell lines other than those examined in Experimental Example 4, expression of Sox2 was confirmed in the same way as in Experimental Example 4 with respect to 14 types of lung cancer cell lines, 3 types of renal cell cancer cell lines, 1 type of prostate cancer cell line, and HeLa cells which are derived from cervical cancer cell line. Fetal brain cells were used as a positive control, and doubly distilled water was used as a negative control. The results are shown in FIG. 6.

Discussion

Expression of Sox2 was confirmed in all of the cancer cell lines examined. This suggests that Sox2 functions as a cancer stem cell molecular marker for far more types of cancer cell lines than other currently known cancer stem cell molecular markers. Furthermore, expression common to a variety of cell lines suggests that Sox2 can become a target for cancer therapy regardless of the part of the body.

EXAMPLE 8

Experimental Example 8

Expression of Smcp in Other Cancer Cells

Figure 7:
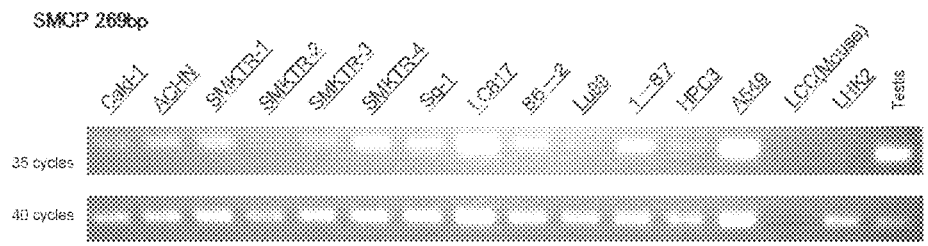
FIG. 7 is a diagram showing expression of Smcp in other cancer cell lines. It shows the results when investigation was carried out by setting the PCR cycles to 35 cycles and 40 cycles respectively. In the diagram, Caki-1, ACHN, and SMKTR-1 to -4 are renal cell cancer cell lines, Sq-1 is a lung squamous cell cancer cell line, 1-87, A549, and LHK2 are lung adenocarcinoma cell lines, LC817 is a lung small cell cancer cell line, 86-2 and Lu99 are lung large cell cancer cell lines, HPC3 is a pancreatic cancer cell line, and LCC (Mouse) is mouse lung cancer cells.

Whether or not Smcp is expressed in other cancer cell lines was examined in detail in the same way as in Experimental Example 5. Expression of Smcp was confirmed in the same way as in Experimental Example 5 using 6 types of renal cell cancer cell lines, 7 types of lung cancer cell lines, and 1 type of prostate cancer cell line as cancer cell lines. Testis cells were used as a positive control, and mouse lung cancer cells were used as a negative control. The results of PCR carried out at cycle numbers of 35 cycles and 40 cycles are shown in FIG. 7.

Discussion

Expression of Smcp was confirmed in all of the cancer cell lines examined. This suggests that, in the same manner as for Sox2, Smcp functions as a molecular marker for far more types of cancer cell lines than known cancer stem cell molecular markers and there is a possibility of its use as a target in therapy.

EXAMPLE 9

Experimental Example 9

Figure 8:
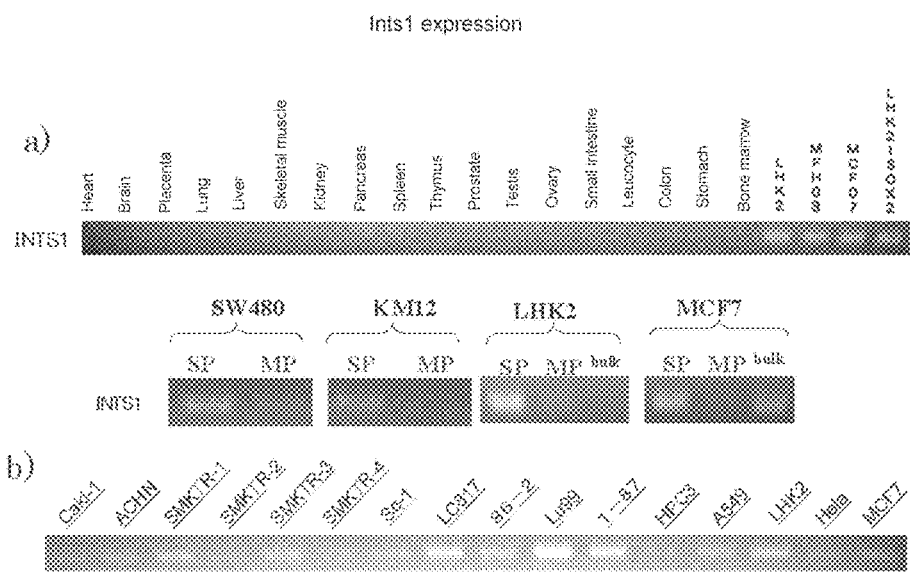
FIG. 8 a) is a diagram showing expression of Ints1 in normal cells and in the SP fraction and MP fraction of cancer cell lines SW480, KM12, LHK2, and MCF7. b) is a diagram showing expression of Ints1 in cancer cell lines. In the diagram, the cancer cell lines are the same as in FIG. 6 and FIG. 7.

Expression of Ints1 in Normal Cells, and Other Cancer Cells, and Cancer Cell Lines a) Expression in Normal Cells and Other Cancer Cells In order to further confirm the usefulness of Ints1, which was confirmed in Experimental Example 3c), expression in human adult normal cells and other cancer cells was examined in the same way as in Experimental Example 5 using Ints1 forward primer and reverse primer (See Table 1). The results are shown in FIG. 8 a).

b) Expression in Other Cancer Cell Lines

Expression of Ints1 in other cancer cell lines was confirmed using the same cell lines as in Experimental Example 8. The results are shown in FIG. 8 b).

Discussion

With regard to normal cells, expression of Ints1 was not confirmed other than very slight expression being observed in the pancreas and spleen. This result suggests that, in almost all tissue, Ints1 is a marker that does not recognize normal cells in tissue, and there is a possibility of tumor cell-specific therapy being carried out in tissue where expression in normal cells was not observed and also, in the pancreas and spleen, where the expression was observed, depending on detection sensitivity. Furthermore, in the same way as in the result of Experimental Example 4, in SW480, KM12, LHK2, and MCF7 also, expression was substantially specific to SP cells, suggesting that it is useful as a cancer stem cell marker.

With regard to other cell lines, expression was confirmed for most cancer cell lines with few exceptions. This suggests that Ints1 functions as a molecular marker for far more types of cancer cell lines than known cancer stem cell molecular markers and there is a possibility of its use as a target in therapy.

EXAMPLE 10

Experimental Example 10

Immunohistochemical Staining of Lung Cancer Tissue Using Anti-SOX2 Antibody

Figure 9:
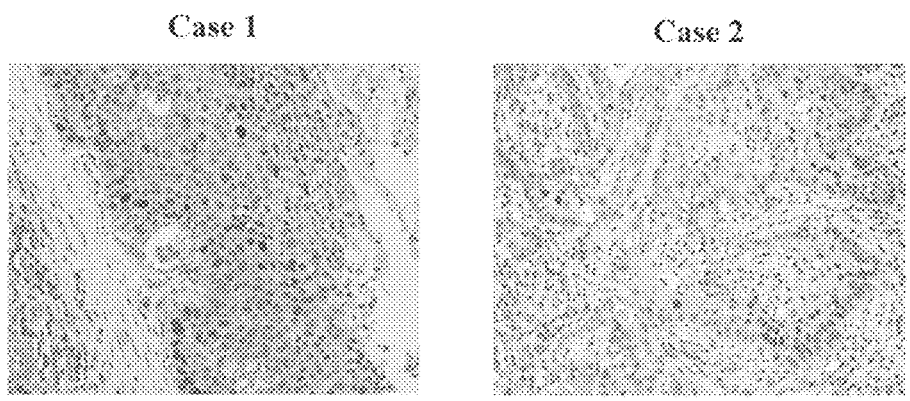
FIG. 9 is a diagram showing the result of immunohistochemical staining in lung cancer tissue. Case 1 and Case 2 are images of stained lung squamous cancer tissue derived from different cancer patients. A blue part denotes a nucleus stained by hematoxylin staining, and a brown part denotes SOX2 antigen protein stained by anti-SOX2 antibody.

Immunohistochemical staining of lung cancer tissue was carried out using an anti-SOX2 polyclonal antibody (ZYMED Inc.). A paraffin-embedded section of human lung cancer fixed by a 20% formalin fixative solution was subjected to a deparaffinization treatment using ethyl alcohol. The section was immersed in a 0.01 mol/L citric acid buffer (pH 6.0) and subjected to autoclaving at 110° C. for 5 minutes to thus carrying out antigen retrieval. 0.5 mL of anti-SOX2 polyclonal antibody was dropped onto the section, and the section was incubated at room temperature for 1 hour. The section was then washed with PBS-T (0.05% Tween 20/PBS, pH 7.4) three times. As a secondary antibody, a peroxidase-labeled anti-mouse IgG antibody (Simple Stain MAX-PO, Nichirei Corporation) was dropped onto the section, and the section was incubated at room temperature for 30 minutes. It was then washed with PBS-T three times. The section was immersed in a mixed liquid of aqueous hydrogen peroxide and DAB substrate (Simple Stain MAX-PO, Nichirei Corporation), thus carrying out a coloring reaction for 1 to 2 minutes. The section was then washed with running water for 1 minute, and subjected to nuclear staining with hematoxylin for 1 to 2 minutes. The results are shown in FIG. 9.

Discussion

SOX2 antigen protein was stained brown. In addition to some of the cells being stained dark brown, a portion corresponding to the tumor invasive edge was stained lightly in a band shape. This result suggests that immunostaining using an anti-SOX2 antibody enables to clarify the morphology, the number and the position of cancer stem cells in lung cancer tissue.

EXAMPLE 11

Experimental Example 11

Immunohistochemical Staining of Breast Cancer Tissue Using Anti-SOX2 Antibody

Figure 10:
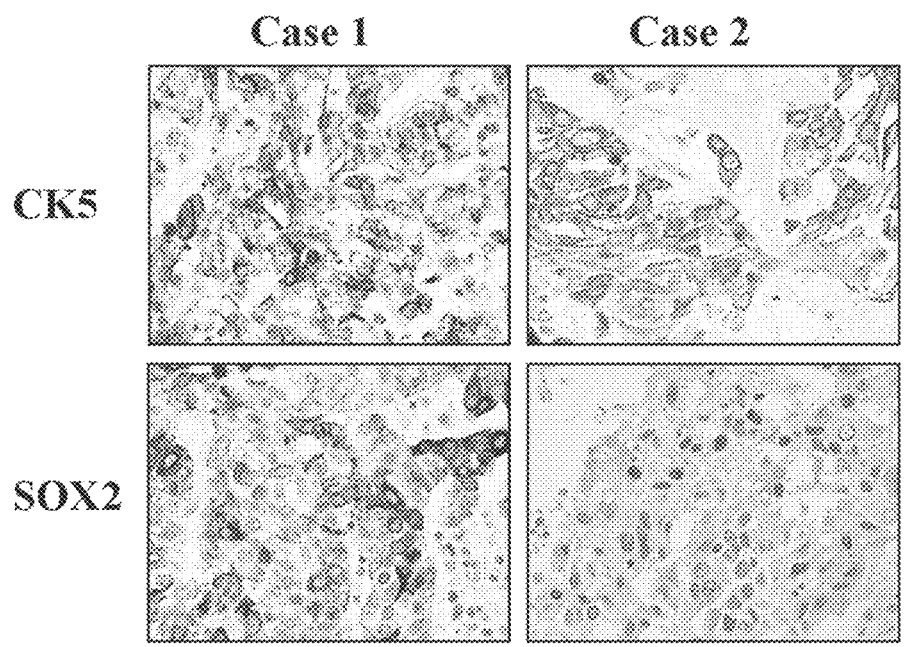
FIG. 10 is a diagram showing the results of immunohistochemical staining in breast cancer tissue. Case 1 shows cytoplasm pattern staining images, Case 2 shows nucleus pattern staining images, CK5 shows images stained by anti-CK5 antibody, and SOX2 shows images stained by anti-SOX2 antibody. A blue part denotes a nucleus stained by hematoxylin staining, and a brown part denotes antigen protein stained by anti-CK5 antibody or anti-SOX2 antibody.

Basaloid type breast cancer tissue was subjected to immunohistochemical staining in the same way as in Experimental Example 10. As a comparative example, staining was also carried out for CK (cytokeratin) 5, which is a basal cell marker. The results are shown in FIG. 10. Brown staining of SOX2 antigen protein was also observed in the breast cancer tissue. This suggests that SOX2 can clarify the morphology, the number and the position of cancer stem cells also in breast cancer. It is generally acknowledged that Basaloid type breast cancer has a poor prognosis and a high metastasis rate, and it is suggested that SOX2 might be involved therein.

EXAMPLE 12

Experimental Example 12

Immunohistochemical Staining of Normal Tissue Using Anti-SOX2 Antibody

Figure 11:
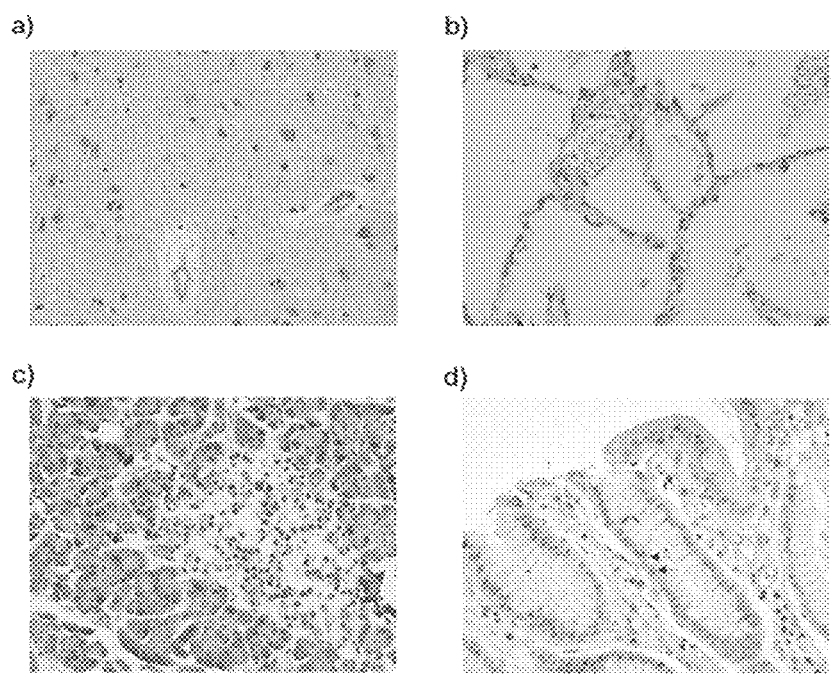
FIG. 11 is a diagram showing the results of immunohistochemical staining in a) brain, b) lung, c) pancreas, and d) stomach. A blue part denotes a nucleus stained by hematoxylin staining, and a brown part denotes SOX2 antigen protein stained by anti-SOX2 antibody. A part shown by black arrow denotes cells slightly stained by SOX2 antibody.

Immunohistochemical staining of normal tissue of the brain, lung, stomach, and pancreas was carried out in the same way as in Experimental Example 10. The results are shown in FIG. 11. A dark stained image of the nucleus was observed in only a very small part of the stomach, but in the other tissue expression was not observed. This shows that SOX2 was hardly expressed in normal tissue.

EXAMPLE 13

Experimental Example 13

Change in Tumorigenic Ability by Forced Expression of SOX2

Figure 12:
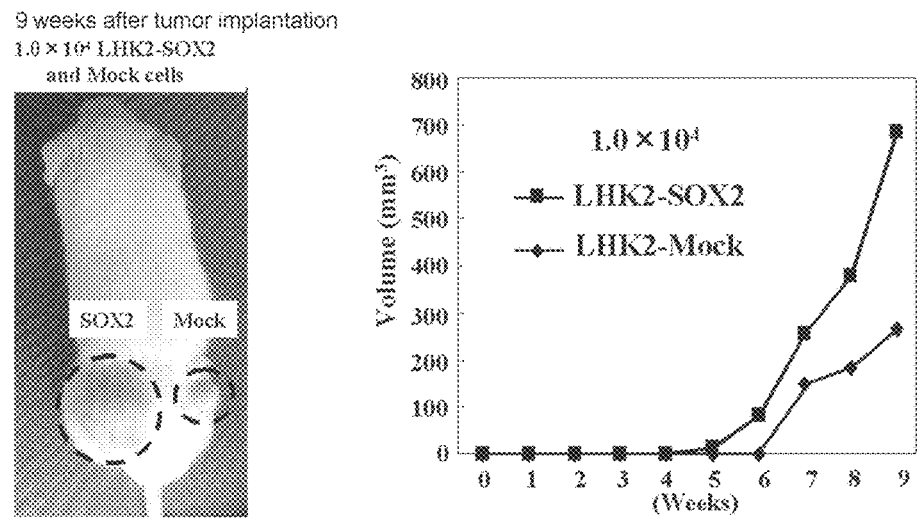
FIG. 12 is a graph showing a change in tumorigenic ability by forced expression of SOX2. The photograph on the left is a photograph of a mouse 9 weeks after tumor implantation. The graph on the right is a graph of average value for tumor size over 9 weeks of a group implanted with 10000 cells. In the graph, the black squares denote LHK2 cells in which SOX2 was forcibly expressed, and the black diamonds denotes mock transfected LHK2 cells.

NOD/SCID mice were inoculated subcutaneously to the left and right dorsal skin with 10000 cells each of cells wherein Sox2 had been forcibly expressed (LHK2-SOX2 cells) and mock transfected cells (LHK2-mock cells) as 100 µL cell-Matrigel mixed liquids; when a tumor started to form, the lengths of the longest diameter and the shortest diameter were measured, and the volume was calculated as approximated to a spheroid and compared. The results are shown in FIG. 12.

Discussion

In tumor tissue where Sox2 had been forcibly expressed, compared with tumor tissue where there was no forced expression thereof, marked tumorigenicity was observed. This result shows that when Sox2 is expressed, cell tumorigenic ability increases. It is thought that this mechanism is related to cancerous transformation of iPS cells.

EXAMPLE 14

Experimental Example 14

Study of Survival Rate of SOX2-Positive Breast Cancer Patients

Figure 13:
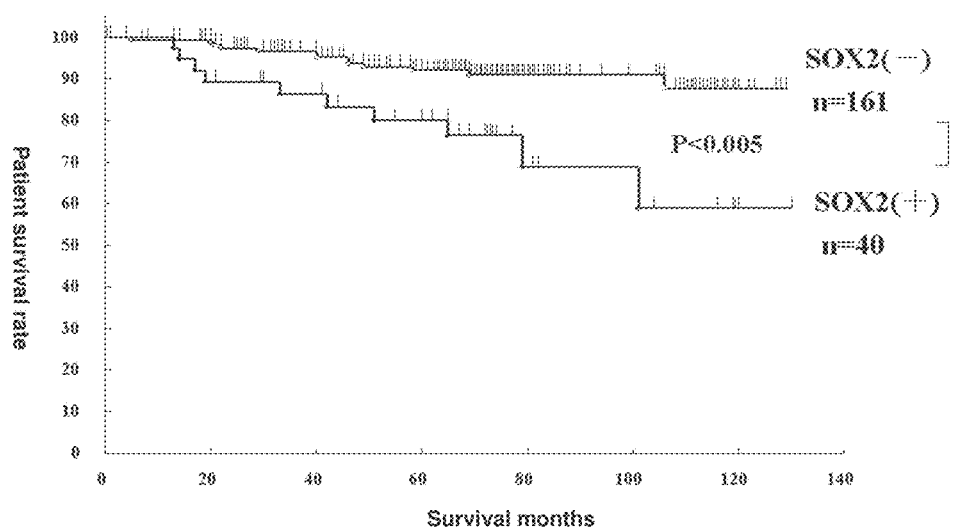
FIG. 13 is a graph showing patient survival rate for SOX2-positive breast cancer patients and SOX2-negative breast cancer patients.

Breast cancer primary tumor tissue was subjected to immunohistochemical staining, and 201 cases of breast cancer were classified into 40 cases of SOX2-positive breast cancer and 161 cases of SOX2-negative breast cancer. FIG. 13 is a graph showing change over time of the survival rate in each classification. SOX2-positive breast cancer patients had significantly lower survival rate compared to SOX2-negative breast cancer patients.

EXAMPLE 15

Experimental Example 15

Figure 14:
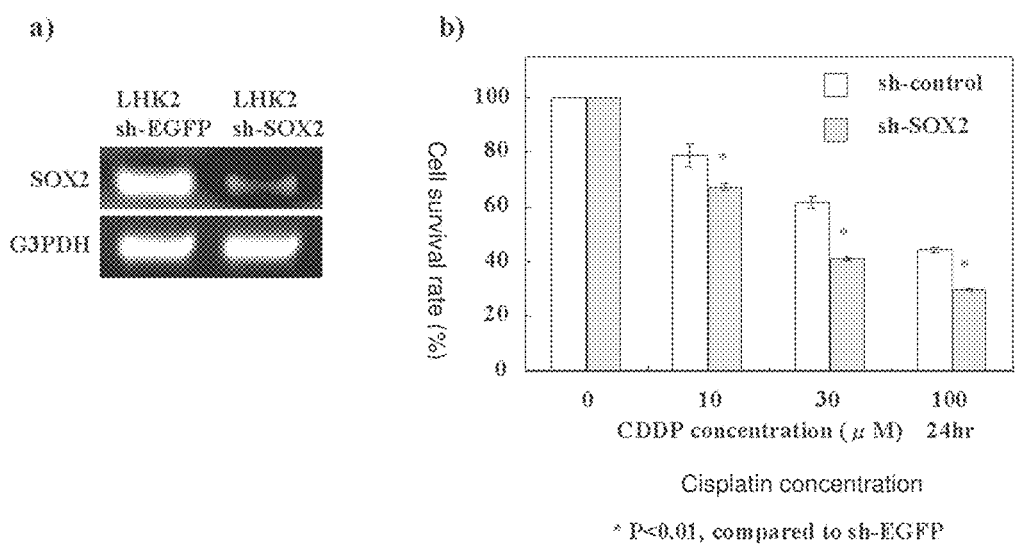
FIG. 14 a) gives the results of investigation of the expression level of SOX2 gene by an RT-PCR method in sh-SOX2 gene transfected cells and sh-EGFP transfected cells. b) is a graph showing cell survival rate at each cisplatin concentration when culturing respective cells in a cisplatin-containing medium for 24 hours.

Suppression of SOX2 Expression sh-SOX2 plasmid and sh-EGFP plasmid were prepared from RNAi-Ready pSIREN-RetroQ vector in accordance with the vector protocol by inserting an annealed oligonucleotide of SEQ ID No: 43, 44 for Sox2 and an annealed oligonucleotide of SEQ ID No: 45, 46 for a negative control as shDNA oligonucleotides. LHK2 cell line was transfected with the sh-SOX2 plasmid and the sh-EGFP plasmid as a negative control and cultured in DMEM medium containing cisplatin at concentrations of 0, 10, 30, and 100 µM at 37° C. for 24 hours. Following this, cell survival rate was measured by an MTT method. The results are shown in FIG. 14.

Discussion

In the sh-SOX2 transfected cells, expression of Sox2 gene was markedly suppressed. Furthermore, compared with cells in which expression of Sox2 gene was not suppressed, the cells in which Sox2 expression was suppressed had significantly lower survival rate when culturing in cisplatin-containing medium. This shows that suppression of expression of Sox2 gene significantly enhanced sensitivity of cells to cisplatin.

EXAMPLE 16

Experimental Example 16

HLA-A24 Peptide Binding Assay of Sox2-Derived Peptide

The amino acid sequence of Sox2 is shown in SEQ ID No: 62. It is known that a peptide that binds to HLA-A24 has tyrosine, tryptophan, phenyl alanine, or methionine as the second amino acid, and the C-terminal amino acid is leucine, isoleucine, tryptophan, phenylalanine, or methionine. Among sequences contained in the amino acid sequence of Sox2, sequences having 9 to 11 amino acids that have this HLA-A24 binding motif were selected, and the peptides below, a total of 13 types, were synthesized.

```
SOX2_1:
                                      (SEQ ID No: 47)
MYNMMETEL

SOX2_50:
                                      (SEQ ID No: 48)
VWSRGQRRKM

SOX2_58:
                                      (SEQ ID No: 49)
KMAQENPKM

SOX2_89:
                                      (SEQ ID No: 50)
PFIDEAKRL

SOX2_109:
                                      (SEQ ID No: 51)
KYRPRRKTKTL

SOX2_119:
                                      (SEQ ID No: 52)
LMKKDKYTL
```

-continued

SOX2_124:
KYTLPGGLL (SEQ ID No: 53)

SOX2_165:
GWSNGSYSM (SEQ ID No: 54)

SOX2_170:
SYSMMQDQL (SEQ ID No: 55)

SOX2_196:
PMHRYDVSAL (SEQ ID No: 56)

SOX2_209:
SMTSSQTYM (SEQ ID No: 57)

SOX2_216:
YMNGSPTYSM (SEQ ID No: 58)

SOX2_226:
SYSQQGTPGM (SEQ ID No: 59)

T2-A24 cell is a cell line in which HLA-A2402 gene has been transferred to human lymphoblastoid T2 cells and expressed. A low level of HLA-A24 molecule is expressed on the cell surface of this cell, and can be detected by a flow cytometer using an HLA-A24 specific monoclonal antibody. The expression level is quantified as a mean fluorescence intensity (MFI). When a synthetic peptide is added to this cell in a test tube, if the peptide added binds to an HLA-A24 molecule, the cell surface HLA-A24 expression level increases in relation to binding affinity. Using this experimental system, the HLA-A24 binding affinity of SOX2-derived cancer antigen peptides of the present invention was analyzed.

T2-A24 cells were cultured at 26° C. overnight. The cells were then washed with PBS; the SOX2-derived synthetic peptide, as positive controls HIV peptide (SEQ ID No: 60), which is a human immunodeficiency virus-derived peptide, and EBV peptide (SEQ ID No: 61), which is an Epstein-Barr virus-derived peptide, and as a negative control SL8 peptide (SEQ ID No: 63), which is an ovalbumin-derived peptide, were added thereto, and cocultured at 26° C. for 3 hours. After cocultured at a temperature of 37° C. for a further 2.5 hours, the cells were centrifuged, supernatant was removed, and the cells were isolated. An anti-HLA-A24 antibody (C7709A2.6) was added to the isolated cells, and the mixture was allowed to stand at 4° C. for 1 hour and then washed with PBS. As a secondary antibody, a fluorescence-labeled anti-mouse IgG+IgM antibody was added, the mixture was allowed to stand at 4° C. for 30 minutes, and the cells were fixed by adding 1% formalin. The fixed cells were subjected to measurement of FITC fluorescence intensity by a flow cytometer (BD FACS Calibur).

Figure 15:
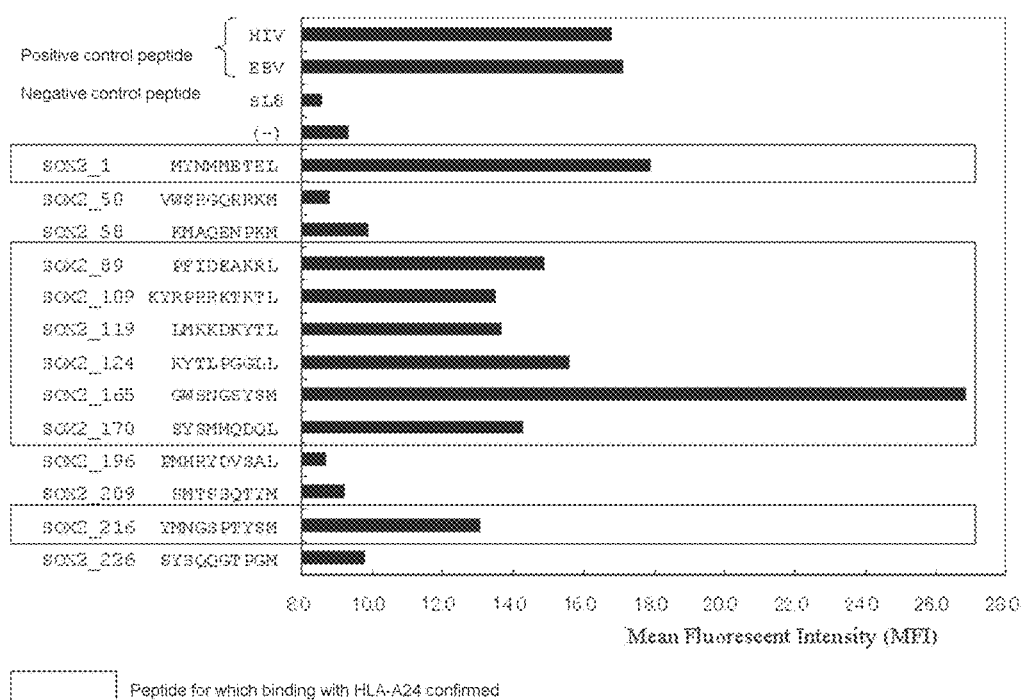
FIG. 15 is a diagram showing the result of an HLA-A24-binding assay of SOX2 polypeptide-derived peptide. A peptide that exhibited an MFI at the same level or close to that of a peptide used as a positive control is identified as an HLA-A24-binding peptide. The sequence identifiers for the sequences in FIG. 15 are as follows: MYNMMETEL (SEQ ID NO: 47), VWSRGQRRKM (SEQ ID NO: 48), KMAQENPKM (SEQ ID NO: 49), PFIDEAKRL (SEQ ID NO: 50), KYRPRRKTKTL (SEQ ID NO: 51), LMKKDKYTL (SEQ ID NO: 52), KYTLPGGLL (SEQ ID NO: 53), GWSNGSYSM (SEQ ID NO: 54), SYSMMQDQL (SEQ ID NO: 55), PMHRYDVSAL (SEQ ID NO: 56), SMTSSQTYM (SEQ ID NO: 57), YMNGSPTYSM (SEQ ID NO: 58), and SYSQQGTPGM (SEQ ID NO: 59).

The results are shown in FIG. 15. Eight SOX2 peptides that exhibited fluorescence intensity at at least the same level as or close to that of the positive controls were determined to be HLA-A24 binding peptides.

EXAMPLE 17

Experimental Example 17

CTL Induction 50 mL of peripheral blood from HLA-A24-positive lung cancer patients who gave informed consent and HLA-A24-positive healthy subjects was centrifuged in a Ficoll-Conray density gradient, and peripheral blood mononuclear cells (PBMC) were separated and collected. Subsequently, lymphocytes of PBMC were separated into CD8-positive lymphocytes and CD8-negative lymphocytes using CD8 MACS beads.

In a 96 well plate, 200000 cells/well of CD8-negative lymphocytes and the above-mentioned HLA-A24 binding SOX2 peptide were mixed, and the mixture was allowed to stand at room temperature for 2 hours, and then subjected to a degree of 100 Gy radiation treatment. The cells thus treated were cocultured with 20 U/mL IL-2 (Takeda Pharmaceutical Company Limited.) and 100000 cells/well CD8-positive lymphocytes, CD8-positive lymphocyte stimulation was carried out once a week for three times in total, and CTLs were induced. The peptide-specific reactivity of the induced CTLs was evaluated by a cytotoxicity assay or an ELISPOT assay.

EXAMPLE 18

Experimental Example 18

Cytotoxicity Assay $Cr^{51}$ was added to T2A24 cells, the cells were cultured in RPMI medium at 37° C. for 1 hour, radiolabeled, and washed with RPMI medium 4 times. Cr-labeled T2A24 was mixed with SOX2 peptide or control peptide (HIV peptide), and the mixture was allowed to stand at room temperature for 1 hour. 2000 cells/well of T2A24 pulsed with SOX2 peptide or control peptide and 14000 cells/well of CD8-positive lymphocytes induced in Example 17 were cocultured in RPMI medium at 37° C. for 4 hours. Supernatant was then collected, and the gamma-ray dose was measured using a gamma counter.

The dose when only RPMI medium and peptide-pulsed T2A24 were cultured was defined as spontaneous release (SPR), the dose when cell lysate (2% NP40) and peptide-pulsed T2A24 were cultured was defined as maximum release (MXR), and cellular cytotoxicity was calculated as (measured value−SPR)/(MXR−SPR)×100.

Figure 16:
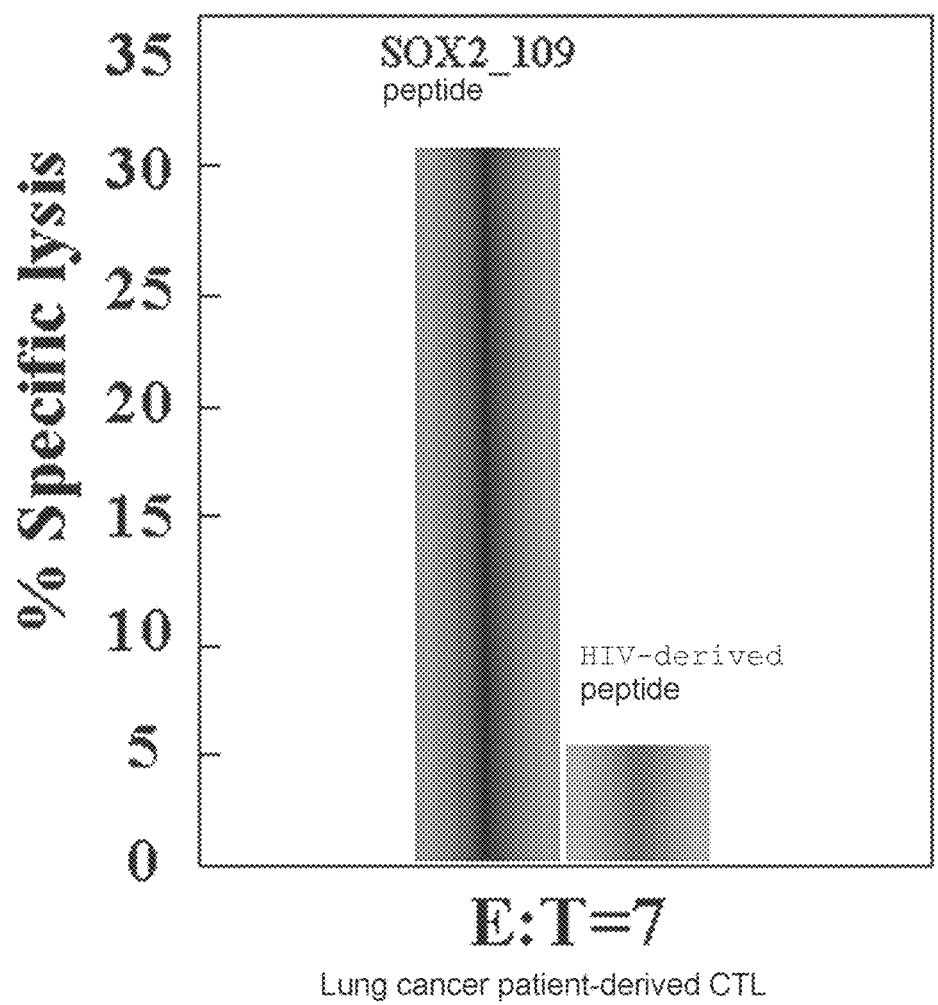
FIG. 16 is a diagram showing the result of a cytotoxicity assay of SOX2_109 peptide (SEQ ID NO: 51). An extremely high level of cytotoxicity was detected relative to HIV-derived peptide, which was a negative control.

From the results, CTLs that specifically damaged T2A24 pulsed with SOX2_109 peptide were detected. The results are shown in FIG. 16. With HIV-derived peptide, which was the control peptide, hardly any radiation due to damaged cells was detected, whereas strong radiation was detected with SOX2_109 peptide.

EXAMPLE 19

Experimental Example 19

ELISPOT Assay

An experiment was carried out using a Human IFNγ ELISPOT set (BD). An ELISPOT plate was coated with an anti-IFNγ antibody by allowing it to stand at 4° C. overnight. SOX2 peptide and a control peptide (HIV peptide) were separately added to T2A24, and the mixtures were allowed to stand at room temperature for 1 hour. 50000 peptide-pulsed T2A24 cells and 10000 CTLs induced in Example 2 were cocultured on the plate coated with anti-IFNγ antibody at 37° C. overnight. After washing with 1×PBS and 0.05% Tween 20, a biotin-labeled anti-IFNγ antibody was added, and the mixture was allowed to stand at room temperature for 2 hours. After washing with 1×PBS and 0.05% Tween 20, HRP-labeled streptavidin was added, and the mixture was allowed to stand at room temperature for 1 hour. After washing with 1×PBS and 0.05% Tween 20, a coloring reagent was added, and the number of spots was counted.

Figure 17:
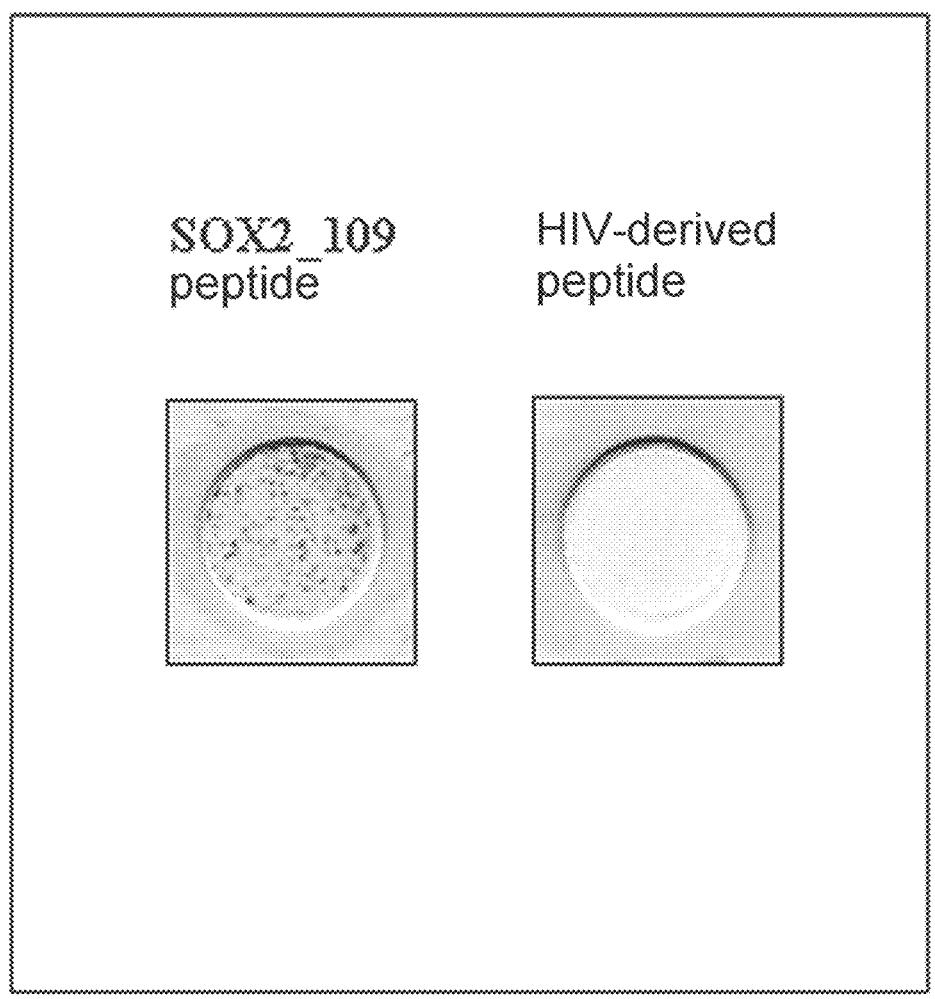
FIG. 17 is a diagram showing the result of an ELISPOT assay of SOX2_109 peptide (SEQ ID NO: 51). Release of IFNγ was not detected for HIV-derived peptide as a negative control, but release of IFNγ was detected for SOX2_109 peptide (SEQ ID NO: 51).

The results are shown in FIG. 17. CTLs that specifically reacted with T2A24 pulsed with SOX2_109 peptide (SEQ ID NO: 51) were detected. It was confirmed that for the HIV-derived peptide, which was a control peptide, release of IFNγ from T cells was not detected, but for SOX2_109 peptide (SEQ ID NO: 51) a large quantity of IFNγ was released.

EXAMPLE 20

Experimental Example 20

Change in Tumorigenicity by Overexpression of SMCP

Figure 18:
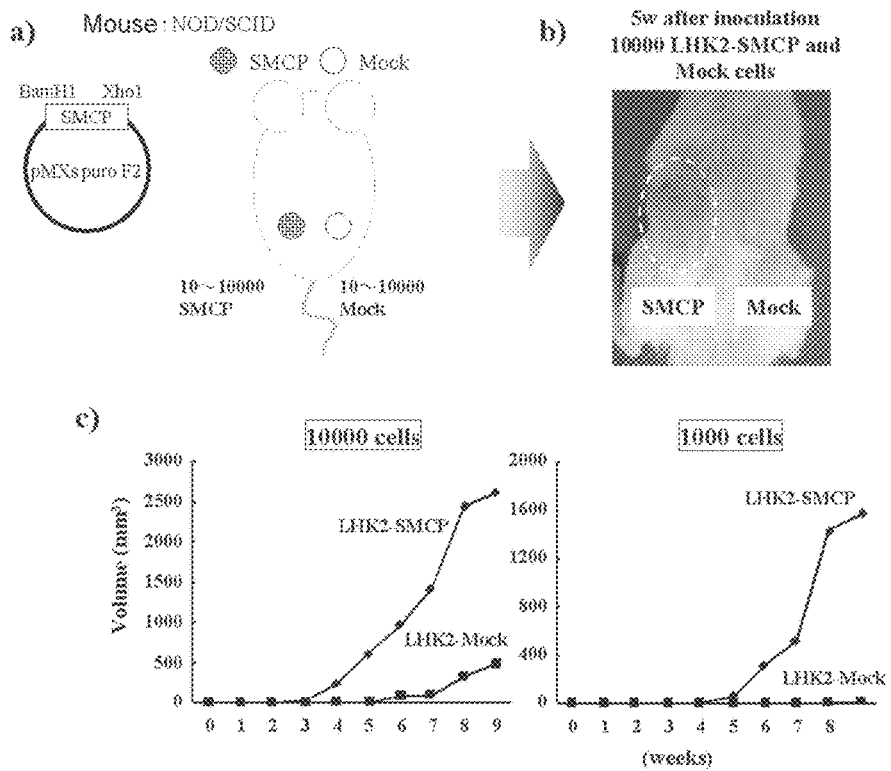
FIG. 18 a) is a schematic diagram of a plasmid used for SMCP gene transfer and a schematic diagram of an implanted mouse, and b) is a photograph of a mouse 5 weeks after SMCP expression gene transfected LHK2 cells and mock transfected LHK2 cells were implanted. c) is a graph of tumor size measured each week after mice were implanted with 1000 and 10000 each of SMCP gene transfected LHK2 cells and mock transfected LHK2 cells. In the graph, the black diamonds denote LHK2 cells in which SMCP gene was forcibly expressed, and the black squares denote mock transfected LHK2 cells.

NOD/SCID mice were inoculated subcutaneously to the left and right dorsal skin with 10000 or 1000 of SMCP-expressing cells (LHK2-SMCP cells) and LHK2-mock cells, as 100 μL of cell-Matrigel mixture; when a tumor started to form, the lengths of the longest diameter and the shortest diameter were measured, and the volume was calculated as approximated to a spheroid and compared. The results are shown in FIG. 18.
Discussion Compared with the mock transfected cells, a large size tumor was formed quickly for the cells in which SMCP was overexpressed. In particular, markedly high tumorigenicity was exhibited even with a small number of cells, and this suggests that SMCP is a gene related to the tumorigenicity of cancer stem cells.

EXAMPLE 21

Experimental Example 21

Suppression of SMCP Expression

Figure 19:
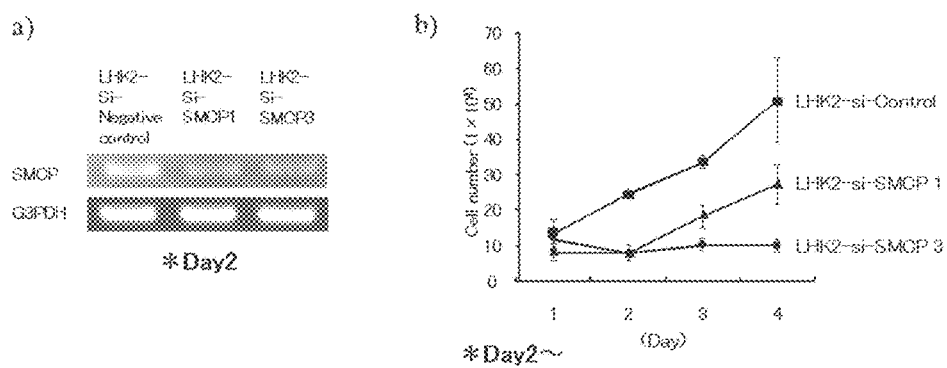
FIG. 19 a) is the result of investigation of expression level of SMCP gene by an RT-PCR method, in two types of siRNA against SMCP transfected cells and 'Stealth RNAi (registered trademark) siRNA Negative Control Hi GC catalog No. 12935-400 (Invitrogen)' transfected cells as a negative control. b) is a graph showing change in the number of cells when respective cells were cultured under the same conditions. In the graph, the black squares denote LHK2 cells as a negative control, the black triangles denote SMCP1 transfected LHK2 cells, and the black circles denote SMCP3 transfected LHK2 cells.
Figure 20:
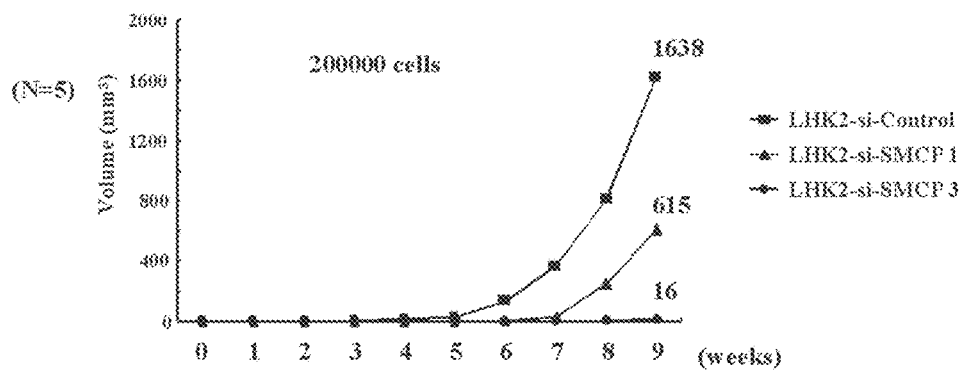
FIG. 20 is a graph of measurement of tumor size each week after NOD/SCID mice were implanted with 200000 cells transfected by each two types of siRNA against SMCP and 'Stealth RNAi (registered trademark) siRNA Negative Control Hi GC catalog No. 12935-400 (Invitrogen)' transfected cells as a negative control, respectively. In the graph, the black squares denote LHK2 cells as a negative control, the black triangles denote SMCP1 transfected LHK2 cells, and the black circles denote SMCP3 transfected LHK2 cells.

As si-RNA, Stealth Select RNAi (registered trademark) siRNA (Catalog#1299003) (Invitrogen) was used. SMCP1 denotes OligoID HSS142897, and SMCP3 denotes OligoID HSS142899. As a negative control, Stealth RNA (registered trademark) siRNA Negative Control Hi GC (12935-400) was used. 100 pmol of si-RNA and 4 μL of Lipofectamine RNAiMAX were mixed, culturing was carried out in a DMEM culture fluid at 37° for 2 days, and mRNA expression level was measured by RT-PCR. The results are shown in FIG. 19a). Furthermore, the increase in the number of cells from 1 day to 4 days after gene transfer was measured. The results are shown in FIG. 19b). 2 days after gene transfer, NOD/SCID mice were inoculated subcutaneously to the left and right dorsal skin with each 200000 of SMCP1 transfected cells (LHK2-si-SMCP1 cells) or SMCP3 transfected cells (LHK2-si-SMCP3 cells), and negative control transfected cells (LHK2-si-control cells), as 100 μL of a cell-Matrigel mixture; when a tumor started to form, the lengths of the longest diameter and the shortest diameter were measured, and the volume was calculated as approximated to a spheroid and compared. The results are shown in FIG. 20.
Discussion Cells in which expression of SMCP gene had been suppressed showed a significant decrease in cell proliferative potential and tumorigenicity. Between si-SMCP1 and si-SMCP3, which are different in part of the sequence, there was a significant difference in the decrease of proliferative potential and tumorigenicity. These results suggests the possibility of treating cancer by suppressing expression of SMCP gene.

EXAMPLE 22

Experimental Example 22

RT-PCR of DNAJB8

DNAJB8 is a member of the DNAJ/HSP40 family and is a gene coding for a 26KD protein, there have been no detailed reports on its localization or function except that it is highly expressed in the testis. It is thought that many of the DNAJ/HSP40 family have a J domain at the N-terminal, and this J domain binds to HSP70 to thus promote hydrolysis of ATP and to bring about a change in the structure of an HSP70 substrate-binding region, thereby controlling HSP70 activity. HSP40 itself has a peptide-binding region, and there is one that has a function of handing over of a peptide to HSP70.

Human Multiple Tissue cDNA Panels I, II (Clontech) were used as normal tissue cDNA, and RNA of cultured cancer cell lines was extracted using an RNeasy Mini Kit (Qiagen). The cultured cancer cell line employed kidney cancer cell lines ACHN, Caki-1, SMKTR2, and SMKTR3, mouse kidney cancer cell line RenCa, bladder cancer cell lines SW780, LB905-BLC, UM-UC3, and T24, prostate cancer cell lines DU145 and LN-CaP, and breast cancer cell line MCF7. cDNA was purified from 2 μg of the extracted RNA using a Superscript III reverse transcription enzyme and an oligo (dT) primer (Invitrogen). PCR was carried out using a total of 20 μL containing 0.25 μg of cDNA, 0.1 μg of Taq DNA polymerase (Qiagen), and 12 pmol of primer. PCR conditions employed the conditions shown in Table 2 of Experimental Example 4b) with 35 cycles. The primer sequences for detecting mouse DNAJB8 were TGACA-GATGGAGAGCAGGTG (SEQ ID No: 64) and CCCTCAT-GAGCTTCTCCTTG (SEQ ID No: 65) for the antisense primer. The size of the PCR product was 408 bp for human DNAJB8 and 463 bp for mouse DNAJB8. The primer sequence of control G3PDH was ACCACAGTCCATGC-CATCAC (SEQ ID No: 66) and TCCACCACCCTGTT-GCTGTA (SEQ ID No: 67) as the antisense primer, and the size of the PCR product was 452 bp.

Figure 21:
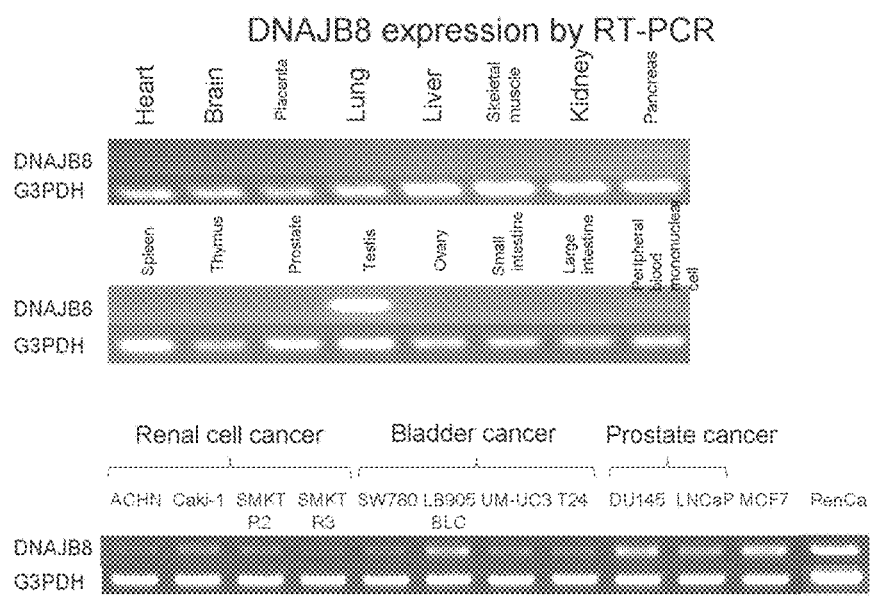
FIG. 21 gives the results of RT-PCR of DNAJB8 in human tissue cells and cultured cancer cells. G3PDH was used as a positive control.

The results are shown in FIG. 21. Apart from being strongly expressed in the testis, hardly any expression of DNAJB8 was observed in human normal cells. On the other hand, in the above-mentioned cultured cancer cell lines, expression was observed in all of the cell lines although there was some degree of difference in the expression level.

EXAMPLE 23

Experimental Example 23

Flow Cytometry Analysis

Figure 22:
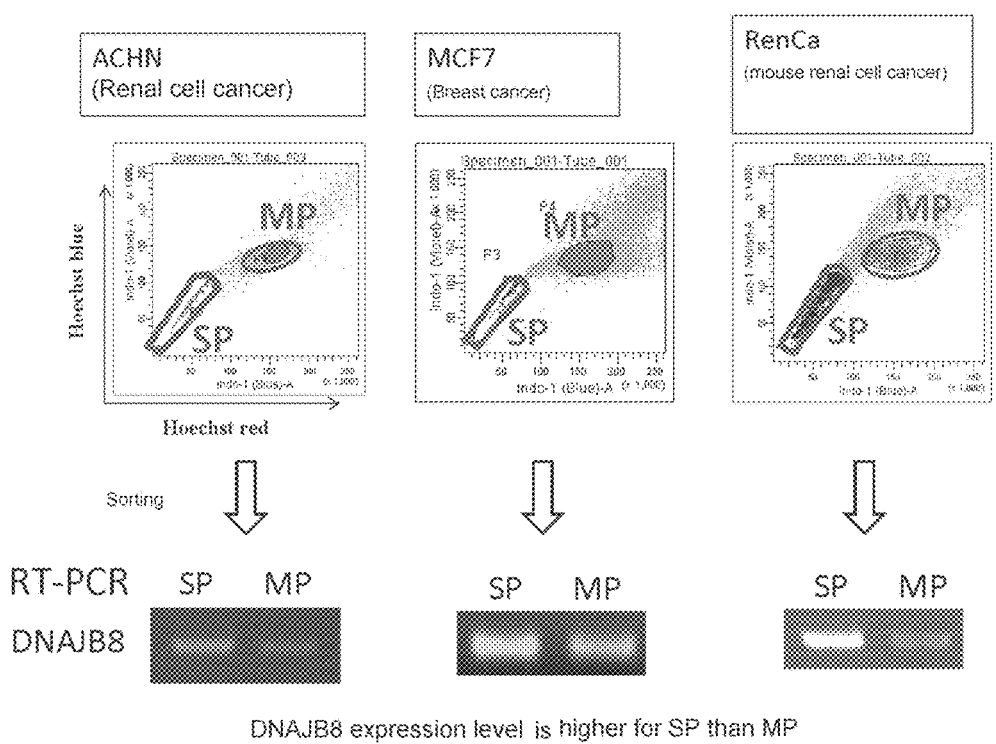
FIG. 22 gives the results of flow cytometry analysis of ACHN, MCF7, and RenCa cells and the results of RT-PCR of DNAJB8 with regard to the SP and MP of the respective cancer cells.

ACHN, MCF7, and RenCa cells were cultured up to a density of 80%, and analysis was carried out by flow cytometry in the same way as in Experimental Example 1. The results are shown in FIG. 22.

An SP fraction was isolated in all of the three types of cell lines, and it was confirmed that expression of DNAJB8 was more intense than for an MP fraction.

EXAMPLE 24

Experimental Example 24

Tumorigenicity Test

Balb/c mice (female, 6 weeks) were inoculated subcutaneously to the left and right dorsal skin with $10^4$, $10^3$, $10^2$, and $10^1$ RenCa cells by the same method as in Experimental Example 2, and the tumor size was measured every week. The tumor volume was calculated as approximated below.

Tumor volume (mm³)=longest diameter (mm)×shortest diameter (mm)² ×½.

Figure 23:
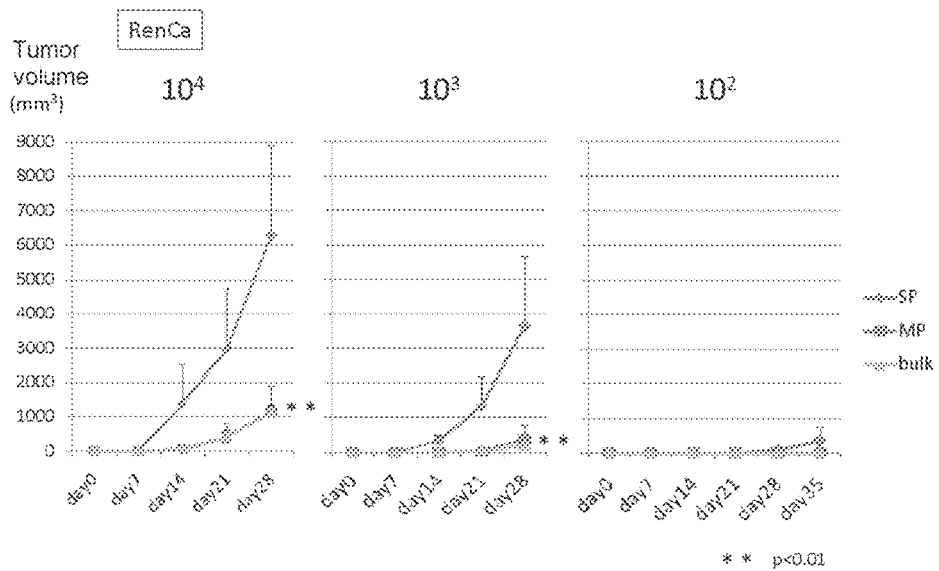
FIG. 23 is a graph showing the relationship between time and tumor volume when rats were implanted with RenCa SP fraction, MP fraction, and unfractionated RenCa.

The results are shown in FIG. 23. SP cells of RenCa exhibited strong tumorigenicity compared with MP cells or cells before cell separation.

EXAMPLE 25

Experimental Example 25

DNA Vaccine Immunoprophylaxis Experiment a) Preparation of DNA Plasmid

Cloning was carried out from RenCa cDNA in order to prepare plasmid expressing DNAJB8 and Survivin, and insertion into the restriction enzyme site between BamHI and XhoI of pcDNA3.1(+) expression vector (Invitrogen) was carried out. On the antigen 5' side, the signal sequence 5'-ATGGAGACAGACACACTCCTGCTATGGGTACT-GCTGCTCTGGGTTCCAGGTTCCACTGGT GAC-3' (SEQ ID NO: 80) of immunoglobulin K chain was inserted into the restriction enzyme site between NheI and HindIII, and on the antigen 3' side, the FLAG sequence 5'-GATTA-CAAGGATGACGACGATAAG-3' (SEQ ID NO: 81) was inserted into the restriction enzyme site between XbaI and PmeI. DNA plasmid was amplified and purified using EndoFree Plasmid Giga kit (Qiagen), and the DNA concentration was measured by the absorbance at 260 nm.

b) Western Blotting

HEK293T cells were cultured up to a density of 70%. An antigen-containing plasmid was gene-transferred to HEK293T cells using FuGENE HD (Roche). After culturing at 37° C. for 48 hours, culture supernatant was collected, centrifuged at 1500 rpm for 5 minutes, and its supernatant was sampled. 0.1 M DTT was added to the supernatant in an amount of 10% of the total amount, and heated at 100° C. for 5 minutes.

The sample was separated by SDS-PAGE on a 12% gel, and transferred to a nitrocellulose membrane. The membrane was blocked, 5000 times diluted primary antibody was added thereto, a reaction was carried out at room temperature for 30 minutes, and a reaction was then carried out using 5000 times diluted peroxidase-labeled secondary antibody at room temperature for 30 minutes. Antigen was identified by chemiluminescence using ECL Western blotting detection reagents (Amersham).

Figure 24:
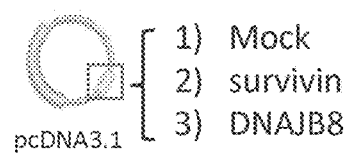
FIG. 24 a) is a map of a plasmid construct. Each mock, survivin, and DNAJB8 sequences has been inserted to the site of square window. b) is the result of Western blotting of a culture supernatant of cells having the plasmid of a) introduced thereinto.
Figure 24:
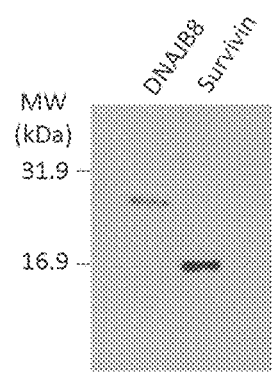

The results are shown in FIG. 24. FIG. 24a) shows a plasmid construct map, the plasmid construct coding for secretory DNAJB8. Furthermore, it has a FLAG-tag sequence at the 3' terminal. FIG. 24b) shows the result of Western blotting. It was thereby found that this plasmid construct expressed secretory DNAJB8 and Survivin.

c) Vaccine Immunoprophylaxis Experiment 5 balb/c mice (6 weeks, female) per group were inoculated via the leg with 200 µg/animal of DNA plasmid vaccine a total of 4 times every week, and inoculated subcutaneously to the dorsal skin with $10^5$/animal of RenCa 1 week after the final inoculation date. The tumor size was measured every week, thus examining the immunogenicity of DNA vaccine.

Figure 25:
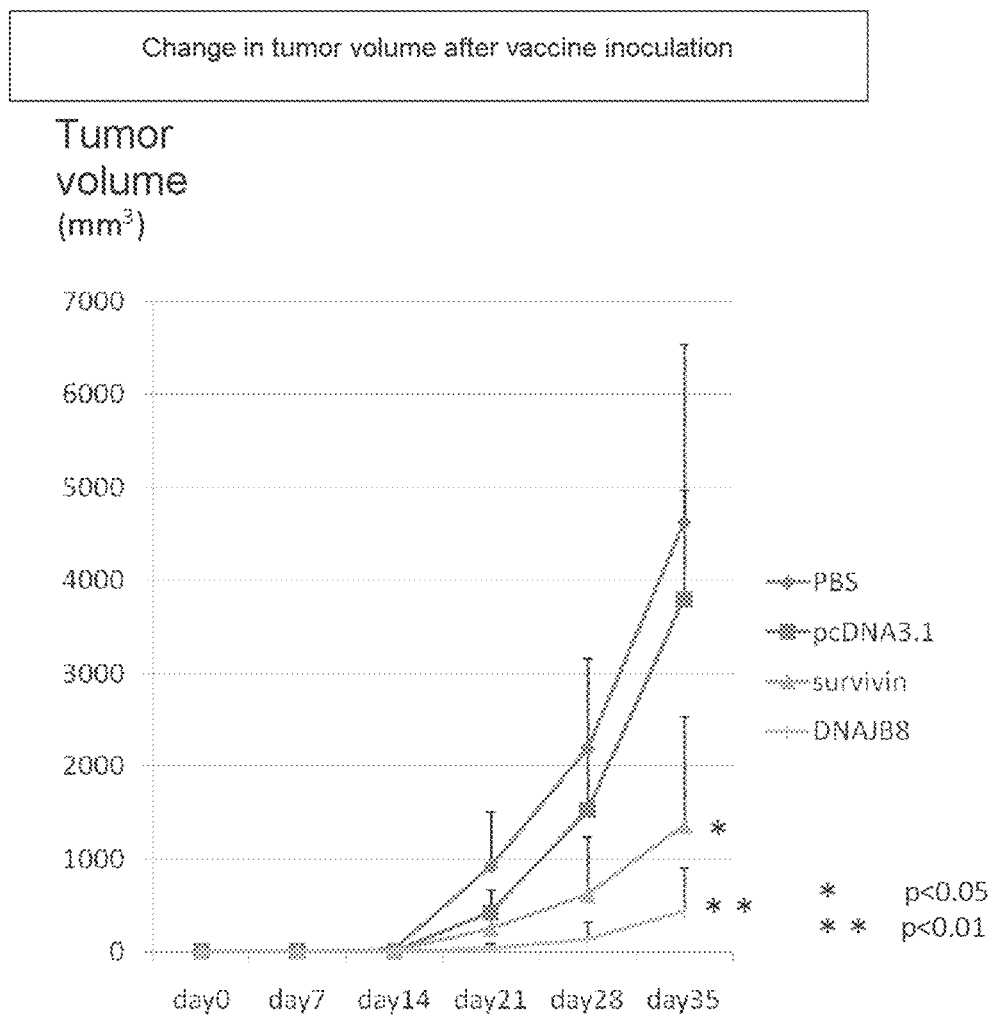
FIG. 25 is a graph showing the relationship between time and implanted tumor volume in mice having plasmid vaccines administered thereto. The circle denote the result of a mouse having PBS administered instead of the vaccine (negative control), the squares denote a mouse having administered a plasmid with nothing inserted thereinto, the triangles denote a mouse having administered a plasmid with survivin inserted thereinto, and the vertical bars denote a mouse having administered plasmid with DNAJB8 inserted thereinto.

The results are shown in FIG. 25. The mice inoculated with DNAJB8 exhibited a significantly greater effect in suppressing increase of the tumor than the mice inoculated with survivin.

EXAMPLE 26

Experimental Example 26

Peptide Binding Assay by DNAJB8-Derived Peptide Fragment

Antigen peptide sequences coded by HLA-A24-restricted DNAJB8 were predicted by BIMAS, and four peptides were prepared.

```
DNAJB8(22-30):
                                    (SEQ ID No: 68)
AYRKLALRW

DNAJB8(90-99):
                                    (SEQ ID No: 69)
GYTFRNPEDI

DNAJB8(99-107):
                                    (SEQ ID No: 70)
IFREFFGGL

DNAJB8(143-151):
                                    (SEQ ID No: 71)
AFMEAFSSF
```

Cell line T2A24 for which HLA-A2402 had been gene-transferred to peptide transporter-deficient T2 cells was used in an assay, and experiment was carried out in the same way as in Experimental Example 16. In this Experimental Example, SL-8 was used as a negative control, and survivin-2B (SEQ ID No: 72) was used as a positive control.

Figure 26:
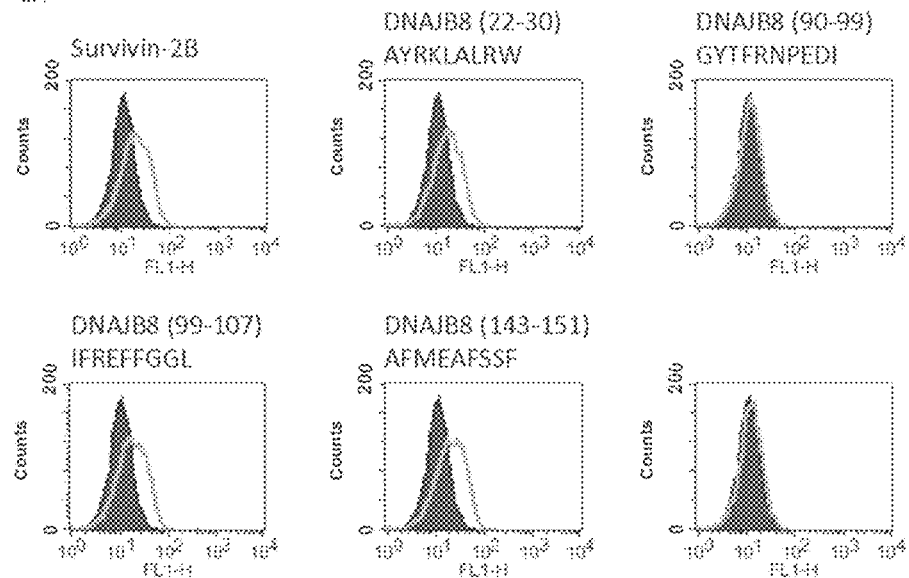
FIG. 26 a) gives graphs showing change in fluorescence of HLA-A24 antibody when exposed to each peptides, and b) is a graph showing mean fluorescence intensity. The sequence identifiers for the sequences in FIG. 26 are as follows: AYRKLALRW (SEQ ID NO: 68), GYTFRNPEDI (SEQ ID NO: 69), IFREFFGGL (SEQ ID NO: 70), and AFMEAFSSF (SEQ ID NO: 71).
Figure 26:
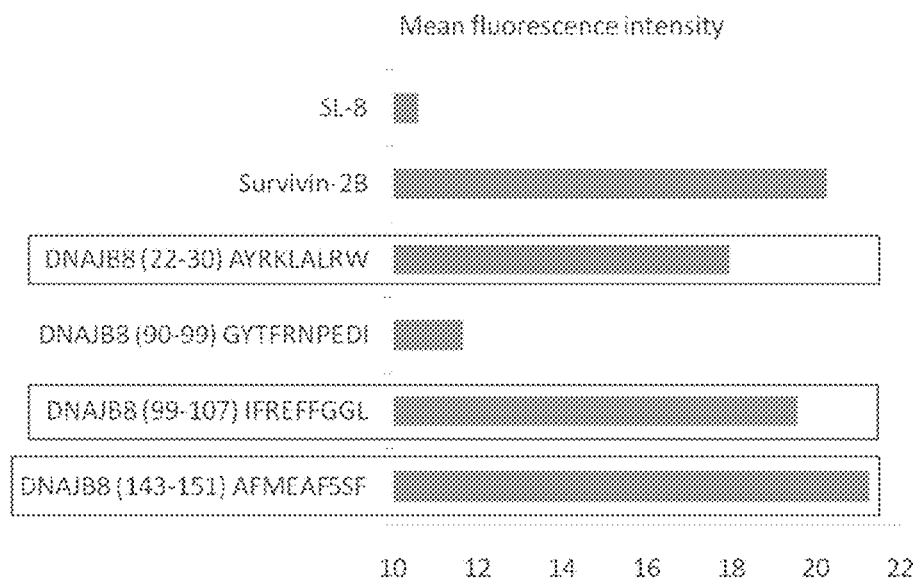

The results are shown in FIG. 26. FIG. 26a) shows the fluorescence transition, and FIG. 26b) shows mean fluorescence intensity. Among the designed four peptides, three exhibited binding to HLA-A24.

EXAMPLE 27

Experimental Example 27

Preparation of DNAJB8 Constitutive Expression Strain

Kidney cancer cell line ACHN was cultured up to 70%, and an antigen was gene-transferred by a retrovirus vector. After culturing at 37° C. for 48 hours, 1 µg/mL of puromycin was added, and cells were selected.

Figure 27:
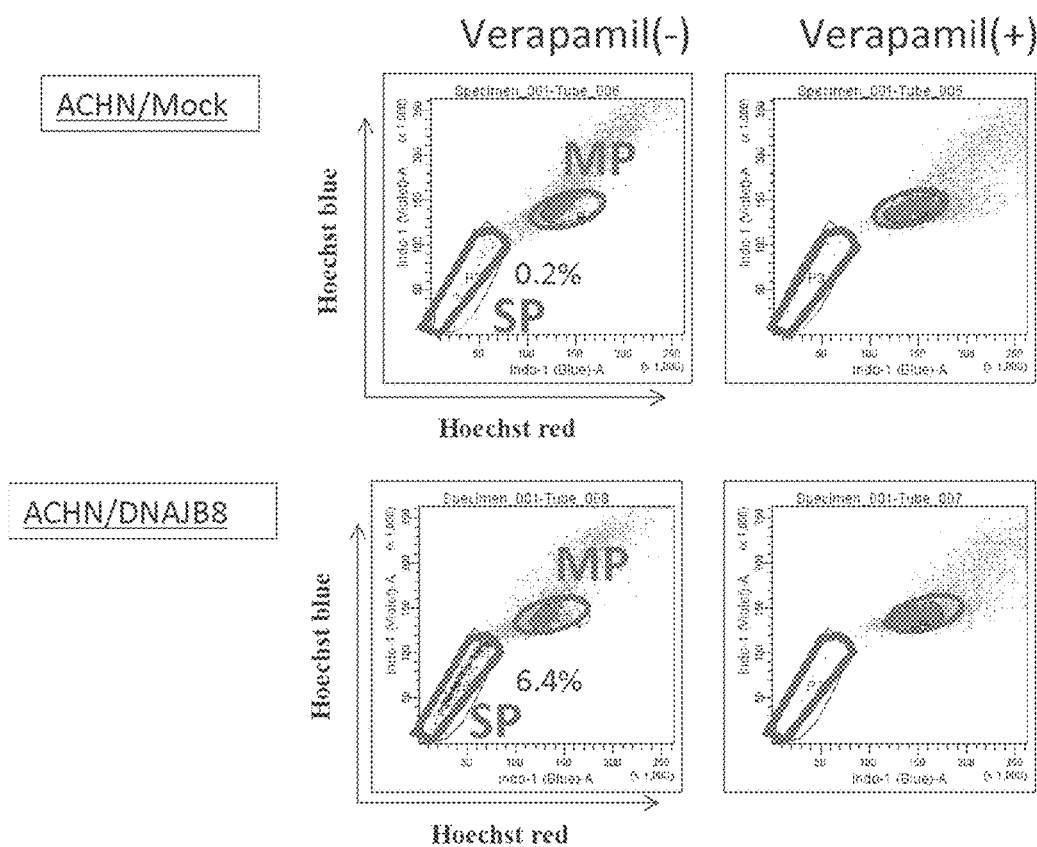
FIG. 27 is a diagram showing change in SP fraction in mock transfected ACHN cells and ACHN cells in which DNAJB8 was forcibly expressed.

The results are shown in FIG. 27. In a cell line that expressed DNAJB8 constitutively, the number of SP fraction cells increased significantly.

EXAMPLE 28

Experimental Example 28

RT-PCR of OR7C1

Olfactory receptor family 7 subfamily C member 1 (OR7C1) is a G protein-coupled seven-transmembrane protein classified as an olfactory receptor family from its structure. Apart from a report of expression on the tongue, there have so far been no detailed reports on a ligand thereof, etc.

Human Multiple Tissue cDNA Panels I, II (Clontech) were used as normal tissue cDNA. RNA of a cultured cancer cell line was extracted using an RNeasy Mini Kit (Qiagen). As cultured cancer cell lines, human large colorectal cancer cell lines Sw480, HT29, HCT15, and KM12LM and human lung cancer cell line LHK2 were used. cDNA was purified from 2 μg of the extracted RNA using Superscript III reverse transcription enzyme and oligo(dT) primer (Invitrogen). PCR was carried out using a total of 20 μL containing 0.25 μg of cDNA, 0.1 μg of Taq DNA polymerase (Qiagen), and 12 pmol of primer. PCR conditions employed the conditions shown in Table 2 of Experimental Example 4b) with 35 cycles. The size of the PCR product was 201 bp.

Figure 28:
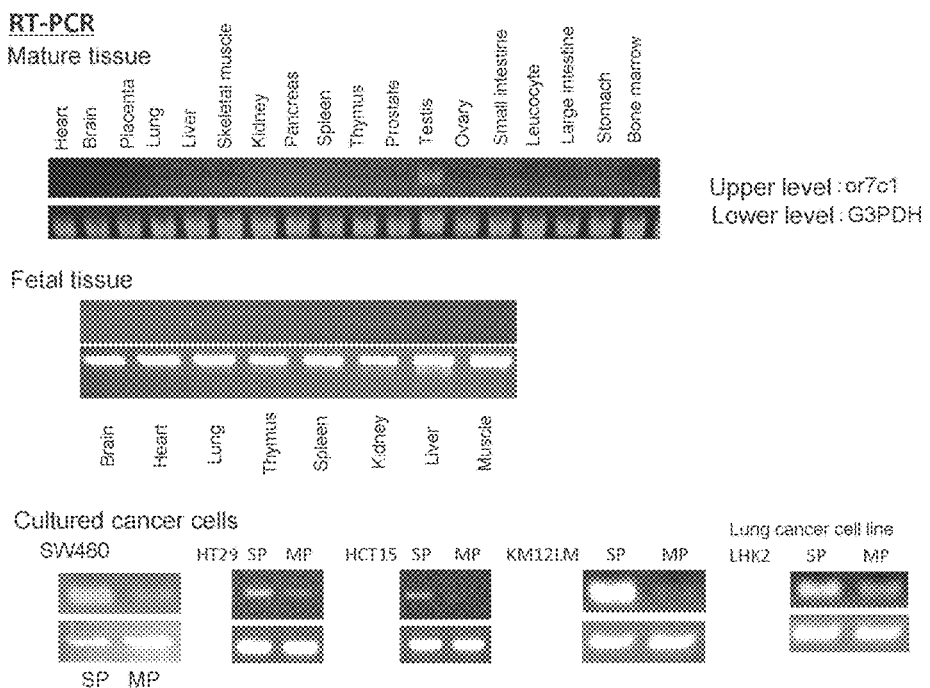
FIG. 28 gives the results of RT-PCR of or7c1 in human mature tissue cells, fetal tissue cells, and cultured cancer cells. G3PDH was used as a positive control.

The results are shown in FIG. 28. Among human mature normal cells and human fetal normal cells, it was only in human mature normal cell testis that OR7C1 was detected. On the other hand, in the SW480 cultured cancer cell line, particularly strong expression was observed in the SP fraction. In the HT29, HCT15, KM12LM, and LHK2 cells also, strong expression was observed in the SP fraction.

EXAMPLE 29

Experimental Example 29

Preparation of or7c1 Constitutive Expression Strain and or7c1 Knockdown Line

PLAT-A cells were cultured up to a density of about 50% in a 10 cm dish with 10% FBS-containing DMEM medium having added thereto 1 μg/mL of puromycin and 10 μg/mL of blasticidin. 10 μg of retrovirus vector pMXs-Ib having or7c1 inserted thereinto +1000 μL of Opti-MEM (Invitrogen) and 40 μL of lipofectamine 2000 (Invitrogen)+1000 μL of Opti-MEM incubated at room temperature for 5 minutes were mixed and incubated at room temperature for a further 20 minutes. Following this, mixing with the above-mentioned PLAT-A cell medium was carried out, culturing was carried out at 37° C., 24 hours thereafter medium exchange with 10% FBS-containing DMEM was carried out, and 24 hours thereafter supernatant was collected as a virus liquid. 1.5 mL of this virus liquid and 8 μg/ml polybrene were cultured in a 6-well plate at 37° C. together with $2 \times 10^5$ Sw480 cells, 8 hours thereafter 1 mL of fresh 10% FBS-containing DMEM was added, and culturing was carried out at 37° C. 48 hours thereafter, 2 μg/mL of puromycin was added, cells were selected, and a constitutive expression strain was obtained.

Preparation of siRNA was contracted to Invitrogen (OR7C1 Stealth Select 3 RNAi (HSS120191; HSS178215; HSS178216), Stealth RNAi Negative control kit). 100 pmol of siRNA+250 μL of Opti-MEM (Invitrogen) and 5 μL of lipofectamine RNAiMAX (Invitrogen)+250 μL of Opti-MEM incubated at room temperature for 5 minutes were mixed, and the mixture was incubated at room temperature for a further 20 minutes. It was then added to a 6 well plate with Sw480 cultured at a density of 20%, culturing was carried out in 10% FBS-containing DMEM at 37° C., and the cells after 48 hours were used as an or7c1 knockdown line.

Figure 29:
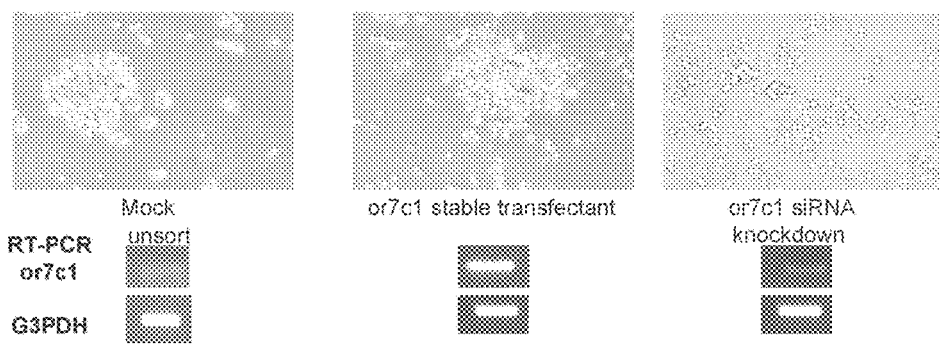
FIG. 29 gives images of the morphology of mock transfected Sw480 cells, Sw480 cells constitutively expressing or7c1, and Sw480 cells having or7c1 knocked down by siRNA observed by a phase contrast microscope, and a diagram showing the results of RT-PCR with respect to or7c1 of the above cells. G3PDH was used as a positive control for RT-PCR.

Phase-contrast microscope images and the results of RT-PCR of or7c1 constitutive expression strain, or7c1 knockdown line, and mock transfected Sw480 cell line as a comparative target are shown in FIG. 29. With regard to the cell morphology, there was no difference in characteristics between the mock transfected Sw480 and the constitutive expression strain, but in the knockdown cell line adhesion between individual cells was lost. It was confirmed from the result of RT-PCR that or7c1 was strongly expressed in the constitutive expression strain, but was hardly expressed in the knockdown line.

Figure 30:
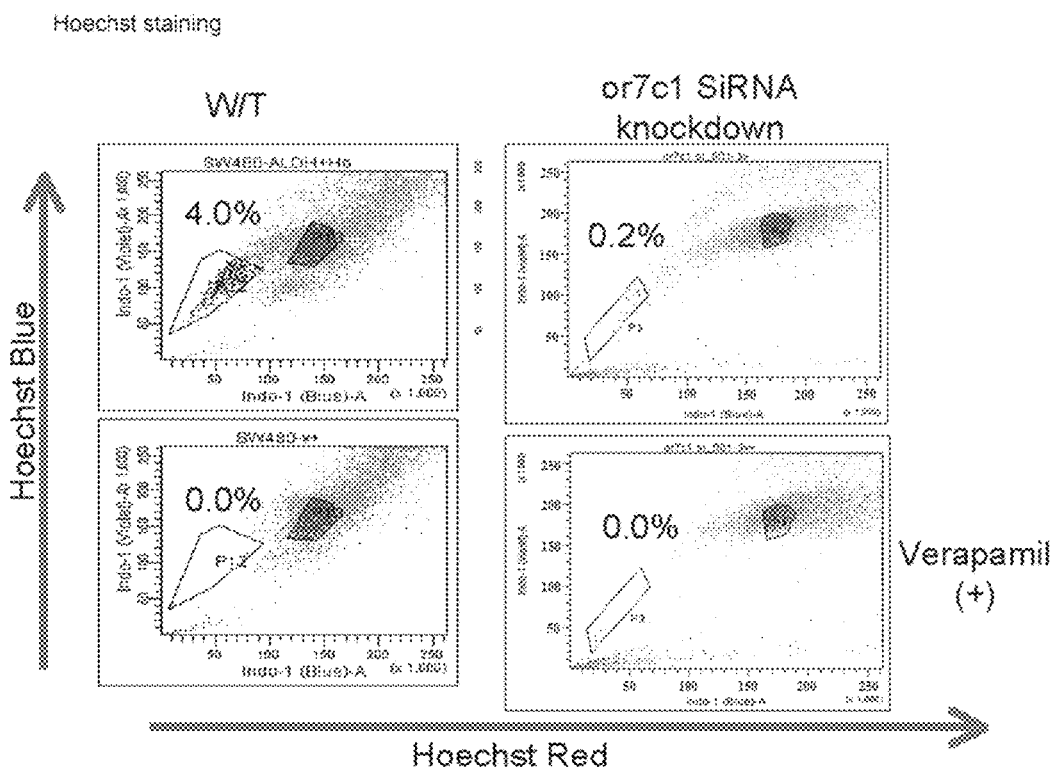
FIG. 30 is a diagram showing the results of flow cytometry analysis with regard to SP fraction of wild type Sw480 cells and Sw480 cells having or7c1 knocked down by siRNA.

Change in the SP fraction of the or7c1 knockdown line was examined in the same way as in Experimental Example 1. The results are shown in FIG. 30. SP cells disappeared in the knockdown cell line.

EXAMPLE 30

Experimental Example 30

Tumorigenicity Test

NOD/SCID mice (female, 5 weeks) were inoculated subcutaneously to the left and right dorsal skin by the same method as in Experimental Example 2 with $10^4$, $10^3$, $10^2$, and $10^1$ tumor cells (or7c1 constitutive expression strain of SW480 cell line) and mock transfected SW480 cells as a negative control, and the tumor size was measured every week. In the same manner, inoculation with $10^4$ or7c1 knockdown cells and negative siRNA line as a negative control was carried out, and the tumor size was measured every week.

Figure 31:
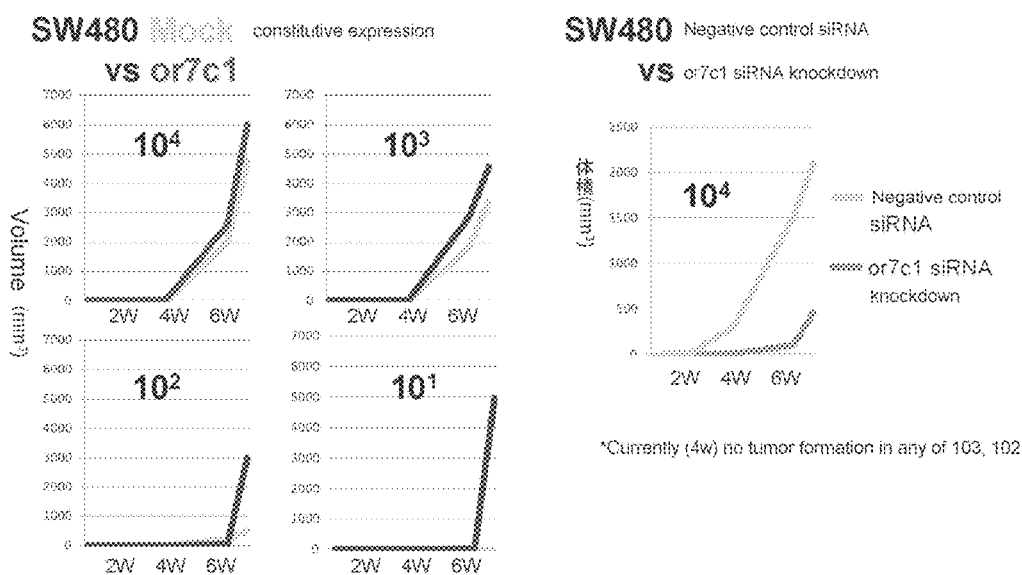
FIG. 31 gives graphs showing change over time in tumor volume when mice were implanted with mock transfected Sw480 cells and Sw480 cells constitutively expressing or7c1, and a graph showing change over time in tumor volume when mice were implanted with cells having or7c1 knocked down by siRNA and cells employing negative siRNA.

The results are shown in FIG. 31. Comparing the mock transfected Sw480 and the or7c1 constitutive expression strain, there was no marked difference for $10^4$ and $10^3$, but for $10^2$ and $10^1$ the tumorigenicity was higher for the constitutive expression strain. With regard to the negative siRNA and the or7c1 knockdown line, for $10^4$ the or7c1 knockdown line exhibited markedly low tumorigenicity.

EXAMPLE 31

Experimental Example 31

Peptide Binding Assay by or7c1-Derived Peptide Fragment

The peptides below were prepared in the same way as in Experimental Example 26, and a binding assay was carried out.

```
or7c1_34(10):
                    (SEQ ID No: 73)
MYLVTFTGNL or7c1_59(10):
                    (SEQ ID No: 74)
MYFF1SNLSF or7c1_93(10):
                    (SEQ ID No: 75)
TYAGCLSQIF or7c1_131(10):
                    (SEQ ID No: 76)
HYTViMNPQL or7c1_217(10):
                    (SEQ ID No: 77)
SYYKiVFSIL or7c1_251(10):
                    (SEQ ID No: 78)
FYGTGFGVYL
```

-continued or7c1_277(9):

(SEQ ID No: 79)

MYTMVTPML

Figure 32:
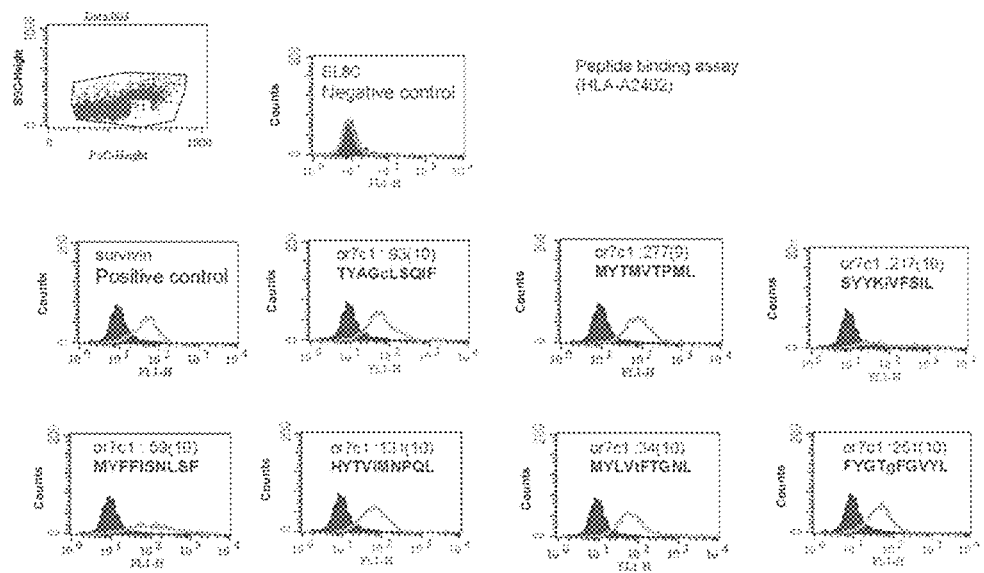
FIG. 32 gives graphs showing change in fluorescence of HLA-A24 antibody when exposed to each peptides. The sequence identifiers for the sequences in FIG. 32 are as follows: TYAGcLSQIF (SEQ ID NO: 75), MYTMVTPML (SEQ ID NO: 79), SYYKiVFSIL (SEQ ID NO: 77), MYF-FlSNLSF (SEQ ID NO: 74), HYTViMNPQL (SEQ ID NO: 76), MYLVtFTGNL (SEQ ID NO: 73), and FYGTgFGVYL (SEQ ID NO: 78).

The results are shown in FIG. 32. From these results, binding to HLA-A2402 was observed for 277(9) (SEQ ID NO: 79), 34(10) (SEQ ID NO: 73), 251(10) (SEQ ID NO: 78), 131(10) (SEQ ID NO: 76), and 93(10) (SEQ ID NO: 75).

EXAMPLE 32

Experimental Example 32

Induction of CTL

PBMC was separated from whole blood (heparin added) sampled from a test subject using Lymphoprep (Nycomed). After PBMC was cultured at 37° C. for 24 hours, an experiment was carried out using non-adherent cells. In order to obtain CD8-positive cells from the non-adherent cells, CD8-positive and -negative cells were separated using a magnetic cell separation system (Miltenyi Biotech). For CD8-negative cells, 100 U/mL IL-2 and 1 µg/mL PHA-P were added to AIM-V medium (Life Technologies) to give PHA-blast. The CD8-positive cells were cultured in AIM-V medium at 37° C. and stimulated with ⅕ the amount of PHA-blast three times every 7 days ($0^{th}$ day, $7^{th}$ day, $14^{th}$ day). From the $8^{th}$ day, 50 U/mL of IL-2 was added to the medium, and thereafter every 3 to 4 days the medium was exchanged, and 50 U/mL of IL-2 was added. The cells were subjected as CTLs to ELISPOT on the $21^{st}$ day and a $^{51}$Cr release assay on the $28^{th}$ day.

EXAMPLE 33

Experimental Example 33

ELISPOT Assay

In order to carry out ELISPOT, $5\times10^5$/mL of the above-mentioned induced CTLs were used as effector cells. T2A24 and K562 cells (K562 being a negative control) were used as a target. T2A24 cells were incubated at room temperature for 2 hours using 5 µg/mL each of peptides that had been found by the above-mentioned peptide binding assay to be presented on HLA-A24. The target cells were adjusted to $5\times10^5$/mL. 100 µL/well of 5 µg/mL IFN-γ capture antibody (PharMingen) was added to a 96 well multiscreen plate (Millipore), and it was immersed in PBS at 4° C. and allowed to stand overnight. The cells were then washed once with 200 µL/well of RPMI1640 (Sigma Chemical Co), and fixed with RPMI1640 for 2 hours. 100 µL each of the above-mentioned effector/target cells were added to the wells, incubated for 40 hours, the cells were removed by washing, and a cytokine antibody for detection was then added. Furthermore, an enzyme-labeled streptavidin was added and counting was carried out using an ELISPOT reader.

Figure 33:
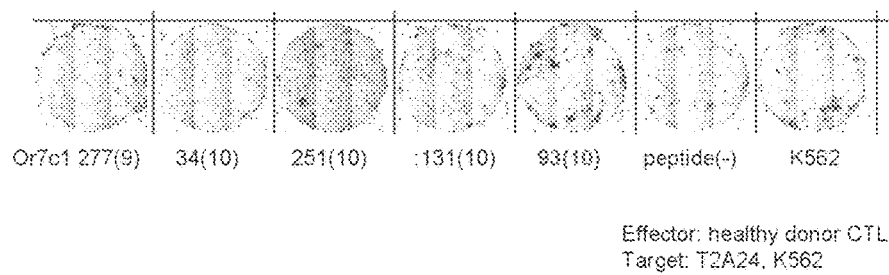
FIG. 33 is a diagram showing the results of ELISPOT assay using peptides for which binding was observed in Experimental Example 32. The sequence identifiers for the sequences in FIG. 33 are as follows: 277(9) (SEQ ID NO: 79), 34(10) (SEQ ID NO: 73), 251(10) (SEQ ID NO: 78), 131(10) (SEQ ID NO: 76), and 93(10) (SEQ ID NO: 75).

The results are shown in FIG. 33. In peptide 93(10) (SEQ ID NO: 75), release of IFN-γ was confirmed.

EXAMPLE 34

Experimental Example 34

$^{51}$Cr Release Assay

In an assay for measuring cellular cytotoxicity, cells were labeled with radioactive $^{51}$Cr, and cellular cytotoxicity by CTLs was measured. CTLs were used as effector cells, and T2A24, K562, Sw480, and Sw480 constitutively expressing or7c1 were used as target cells. First, $1\times10^6$ target cells were collected, 10 to 100 µL of $^{51}$Cr was added, and incubated at 37° C. for 1 hour, thus labeling the cells with $^{51}$Cr. The labeled cells were washed with RPMI1640 four times, and dissolved in RPMI1640 so as to give $1\times10^5$/mL (finally used at 2000 target cells/well). T2A24 was pulsed with 5 µg/mL of peptide, and incubated at room temperature for 1 hour. On the other hand, CTLs were plated in a 96 well plate by dissolving with 100 µL of AMI-V according to respective E/T ratios. For analysis of data, 100 µL of AIM-V in a well for measuring spontaneous release and 100 µL of 2% NP-40 in a well for measuring maximum release were placed in advance in wells. 100 µL each of the target cells were added to wells of a 96 well plate containing the effector, and cultured at 37° C. for 4 hours. Culture supernatants were then collected and subjected to measurement using a gamma counter. Analysis employed the equation below.

Kill %=(measured release−spontaneous release)×100/ (maximum release−spontaneous release)

Figure 34:
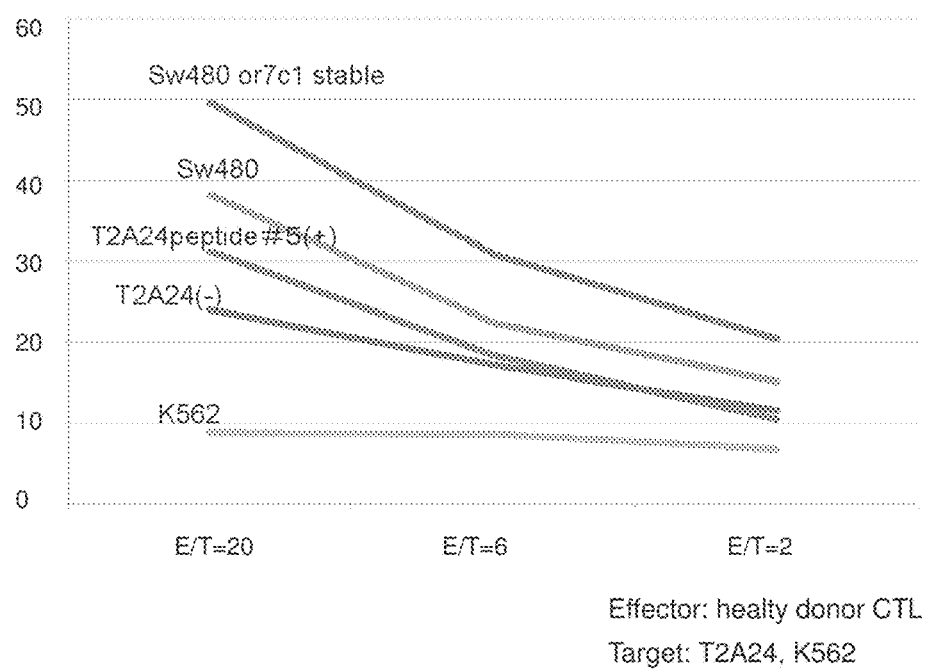
FIG. 34 is a graph showing the relationship between E/T ratio and kill rate in a $^{51}Cr$ release assay.

The results are shown in FIG. 34. Compared with Sw480, the cellular cytotoxicity was higher for Sw480 constitutively expressing or7c1. With regard to T2A24, for E/T ratios of 20 and 6, one pulsed with peptide 93(10) (SEQ ID NO: 75) exhibited higher cellular cytotoxicity.

INDUSTRIAL APPLICABILITY

The molecular marker provided by the present invention for use in a determination method is usually hardly expressed in adult normal cells but is expressed in many cancer stem cells, and enables a much higher precision diagnosis than conventional cancer diagnosis techniques by specifically recognizing only tumor cells in body or tissue. Furthermore, since it specifically recognizes cancer stem cells in particular, it is expected that it will widely contribute to the medical industry, such as in the development of cancer immunotherapy, molecular target therapy, gene transfer therapy, etc.

The invention claimed is:

1. A method for treating a subject having a tumor comprising administering to the subject an effective amount of any of (i) to (iii) below:
   (i) Or7c1 93: TYAGCLSQIF (SEQ ID NO: 75);
   (ii) a peptide in which the second amino acid from the N terminal of the peptide of (i) is replaced by tryptophan, phenylalanine or methionine, and/or the amino acid at the C terminal of the peptide of (i) is replaced by leucine, isoleucine, tryptophan or methionine, wherein said peptide has HLA-A24 binding ability; or
   (iii) a peptide in which one amino acid is added to the N or C terminus of the peptide of (i) or the peptide of (ii), wherein said peptide has HLA-A24 binding ability.

2. The method according to claim 1, wherein the peptide (i) or (ii) is administered to the subject.

3. The method according to claim 2, wherein the peptide is Or7c1_93: TYAGCLSQIF (SEQ ID NO: 75).

* * * * *

SEQUENCE LISTING

<160> NUMBER OF SEQ ID NOS: 81

<210> SEQ ID NO 1
<211> LENGTH: 20
<212> TYPE: DNA
<213> ORGANISM: Artificial

```
<220> FEATURE:
<223> OTHER INFORMATION: forward primer for Homo Sapiens SRY(Sex
      determining region Y)-box 2, mRNA

<400> SEQUENCE: 1
acttttgtcg gagacggaga                                                  20

<210> SEQ ID NO 2
<211> LENGTH: 20
<212> TYPE: DNA
<213> ORGANISM: Artificial
<220> FEATURE:
<223> OTHER INFORMATION: reverse primer for Homo sapiens SRY(Sex
      determining region Y)-box 2, mRNA

<400> SEQUENCE: 2
gttcatgtgc gcgtaactgt                                                  20

<210> SEQ ID NO 3
<211> LENGTH: 22
<212> TYPE: DNA
<213> ORGANISM: Artificial
<220> FEATURE:
<223> OTHER INFORMATION: forward primer for Homo sapiens sperm
      mitochondria-associated cysteine-rich protein, mRNA

<400> SEQUENCE: 3
tgtgtgacca gacaaaacac ag                                               22

<210> SEQ ID NO 4
<211> LENGTH: 20
<212> TYPE: DNA
<213> ORGANISM: Artificial
<220> FEATURE:
<223> OTHER INFORMATION: reverse primer for Homo sapiens sperm
      mitochondria-associated cysteine-rich protein, mRNA

<400> SEQUENCE: 4
gttgggctca gactccatgt                                                  20

<210> SEQ ID NO 5
<211> LENGTH: 20
<212> TYPE: DNA
<213> ORGANISM: Artificial
<220> FEATURE:
<223> OTHER INFORMATION: forward primer for Homo sapiens integrator
      complex subunit 1, mRNA

<400> SEQUENCE: 5
tgtccagcat gagcaaactc                                                  20

<210> SEQ ID NO 6
<211> LENGTH: 20
<212> TYPE: DNA
<213> ORGANISM: Artificial
<220> FEATURE:
<223> OTHER INFORMATION: reverse primer for Homo sapiens integrator
      complex subunit 1, mRNA

<400> SEQUENCE: 6
aaaccgtagc agggtcacac                                                  20

<210> SEQ ID NO 7
<211> LENGTH: 20
<212> TYPE: DNA
<213> ORGANISM: Artificial
```

```
<220> FEATURE:
<223> OTHER INFORMATION: forward primer for Homo sapiens zinc finger
      protein 19, mRNA

<400> SEQUENCE: 7
atgtggaaaa gcaccaggac                                              20

<210> SEQ ID NO 8
<211> LENGTH: 20
<212> TYPE: DNA
<213> ORGANISM: Artificial
<220> FEATURE:
<223> OTHER INFORMATION: reverse primer for Homo sapiens zinc finger
      protein 19, mRNA

<400> SEQUENCE: 8
tcctctggtg ccgaattaac                                              20

<210> SEQ ID NO 9
<211> LENGTH: 20
<212> TYPE: DNA
<213> ORGANISM: Artificial
<220> FEATURE:
<223> OTHER INFORMATION: forward primer for Homo sapiens Myo-D family
      inhibitor, mRNA

<400> SEQUENCE: 9
caggaagact gctgtgtcca                                              20

<210> SEQ ID NO 10
<211> LENGTH: 20
<212> TYPE: DNA
<213> ORGANISM: Artificial
<220> FEATURE:
<223> OTHER INFORMATION: reverse primer for Homo sapiens Myo-D family
      inhibitor, mRNA

<400> SEQUENCE: 10
atgcagatct ccaggcagtc                                              20

<210> SEQ ID NO 11
<211> LENGTH: 20
<212> TYPE: DNA
<213> ORGANISM: Artificial
<220> FEATURE:
<223> OTHER INFORMATION: forward primer for Homo sapiens cDNA FLJ13464

<400> SEQUENCE: 11
tgcataacac caaaggtcca                                              20

<210> SEQ ID NO 12
<211> LENGTH: 20
<212> TYPE: DNA
<213> ORGANISM: Artificial
<220> FEATURE:
<223> OTHER INFORMATION: reverse primer for Homo sapiens cDNA FLJ13464

<400> SEQUENCE: 12
gacctggcca atacaatgct                                              20

<210> SEQ ID NO 13
<211> LENGTH: 20
<212> TYPE: DNA
<213> ORGANISM: Artificial
<220> FEATURE:
<223> OTHER INFORMATION: forward primer for Homo sapiens cDNA
      DKFZp667J237
```

-continued

```
<400> SEQUENCE: 13
aggacatgcc tgggtgatag                                                   20

<210> SEQ ID NO 14
<211> LENGTH: 20
<212> TYPE: DNA
<213> ORGANISM: Artificial
<220> FEATURE:
<223> OTHER INFORMATION: reverse primer for Homo sapiens cDNA
      DKFZp667J237

<400> SEQUENCE: 14
cccaatcctg agttcttcca                                                   20

<210> SEQ ID NO 15
<211> LENGTH: 20
<212> TYPE: DNA
<213> ORGANISM: Artificial
<220> FEATURE:
<223> OTHER INFORMATION: forward primer for Homo sapiens surfeit 6, mRNA

<400> SEQUENCE: 15
cgactgcatg agaagatcca                                                   20

<210> SEQ ID NO 16
<211> LENGTH: 20
<212> TYPE: DNA
<213> ORGANISM: Artificial
<220> FEATURE:
<223> OTHER INFORMATION: reverse primer for Homo sapiens surfeit 6, mRNA

<400> SEQUENCE: 16
gaggaggttg gtccacttca                                                   20

<210> SEQ ID NO 17
<211> LENGTH: 20
<212> TYPE: DNA
<213> ORGANISM: Artificial
<220> FEATURE:
<223> OTHER INFORMATION: forward primer for Homo sapiens protocadherin
      19, transcript variant 1, mRNA

<400> SEQUENCE: 17
cccaaggtca acagcgttat                                                   20

<210> SEQ ID NO 18
<211> LENGTH: 20
<212> TYPE: DNA
<213> ORGANISM: Artificial
<220> FEATURE:
<223> OTHER INFORMATION: reverse primer for Homo sapiens protocadherin
      19, transcript variant 1, mRNA

<400> SEQUENCE: 18
cacaccaggg gactctttgt                                                   20

<210> SEQ ID NO 19
<211> LENGTH: 20
<212> TYPE: DNA
<213> ORGANISM: Artificial
<220> FEATURE:
<223> OTHER INFORMATION: forward primer for Homo sapiens dachsous 2
      (Drosphila), transcript cariant 1, mRNA

<400> SEQUENCE: 19
gaaggagatc aaggggaagg                                                   20
```

<210> SEQ ID NO 20
<211> LENGTH: 20
<212> TYPE: DNA
<213> ORGANISM: Artificial
<220> FEATURE:
<223> OTHER INFORMATION: reverse primer for Homo sapiens dachsous 2
      (Drosophila), transcript variant 1,mRNA

<400> SEQUENCE: 20
atcaaagggg gtggaaaaac                                              20

<210> SEQ ID NO 21
<211> LENGTH: 20
<212> TYPE: DNA
<213> ORGANISM: Artificial
<220> FEATURE:
<223> OTHER INFORMATION: forward primer for homo sapiens protocadherin
      21, mRNA

<400> SEQUENCE: 21
atgcagagga acccaacaac                                              20

<210> SEQ ID NO 22
<211> LENGTH: 20
<212> TYPE: DNA
<213> ORGANISM: Artificial
<220> FEATURE:
<223> OTHER INFORMATION: reverse primer for Homo sapiens protocadherin
      21, mRNA

<400> SEQUENCE: 22
tgagtaaggc tgtggtgctg                                              20

<210> SEQ ID NO 23
<211> LENGTH: 20
<212> TYPE: DNA
<213> ORGANISM: Artificial
<220> FEATURE:
<223> OTHER INFORMATION: forward primer for Homo sapiens galactose-3-O-
      sulfotransferase 1, mRNA

<400> SEQUENCE: 23
ggcctgcttc aacatcatct                                              20

<210> SEQ ID NO 24
<211> LENGTH: 20
<212> TYPE: DNA
<213> ORGANISM: Artificial
<220> FEATURE:
<223> OTHER INFORMATION: reverse primer for Homo sapiens galactose-3-
      sulfotransferase 1, mRNA

<400> SEQUENCE: 24
gctgttgtca tagcccaggt                                              20

<210> SEQ ID NO 25
<211> LENGTH: 20
<212> TYPE: DNA
<213> ORGANISM: Artificial
<220> FEATURE:
<223> OTHER INFORMATION: forward primer for Homo sapiens ras-like family
      11, member B, mRNA

<400> SEQUENCE: 25
tgtggtgatc gttttctcca                                              20

```
<210> SEQ ID NO 26
<211> LENGTH: 20
<212> TYPE: DNA
<213> ORGANISM: Artificial
<220> FEATURE:
<223> OTHER INFORMATION: reverse primer for Homo sapiens ras-like family
      11, member B, mRNA

<400> SEQUENCE: 26
agggaggttc ttcgcttctc                                           20

<210> SEQ ID NO 27
<211> LENGTH: 20
<212> TYPE: DNA
<213> ORGANISM: Artificial
<220> FEATURE:
<223> OTHER INFORMATION: forward primer for Homo sapiens hairy and
      enhancer of split 6 (Drosophila), mRNA

<400> SEQUENCE: 27
agctcctgaa ccatctgctc                                           20

<210> SEQ ID NO 28
<211> LENGTH: 20
<212> TYPE: DNA
<213> ORGANISM: Artificial
<220> FEATURE:
<223> OTHER INFORMATION: reverse primer for Homo sapiens hairy and
      enhancer of split 6 (Drosophila), mRNA

<400> SEQUENCE: 28
agcaggagcc tgactcagtt                                           20

<210> SEQ ID NO 29
<211> LENGTH: 20
<212> TYPE: DNA
<213> ORGANISM: Artificial
<220> FEATURE:
<223> OTHER INFORMATION: forward primer for Homo sapiens zinc finger
      protein 415, mRNA

<400> SEQUENCE: 29
cttgcaaggc attggagaat                                           20

<210> SEQ ID NO 30
<211> LENGTH: 20
<212> TYPE: DNA
<213> ORGANISM: Artificial
<220> FEATURE:
<223> OTHER INFORMATION: reverse primer for Homo sapiens zinc finger
      protein 415, mRNA

<400> SEQUENCE: 30
taggcttgaa tgcacactga                                           20

<210> SEQ ID NO 31
<211> LENGTH: 20
<212> TYPE: DNA
<213> ORGANISM: Artificial
<220> FEATURE:
<223> OTHER INFORMATION: forward primer for Homo sapiens NK2
      transcription factor related, locus 5 (Drosophila), mRNA

<400> SEQUENCE: 31
acgcccttct cagtcaaaga                                           20
```

<210> SEQ ID NO 32
<211> LENGTH: 20
<212> TYPE: DNA
<213> ORGANISM: Artificial
<220> FEATURE:
<223> OTHER INFORMATION: reverse primer for Homo sapiens NK2
      transcription factor related, locus 5 (Drosophila), mRNA

<400> SEQUENCE: 32
ttttcggctc tagggtcctt                                              20

<210> SEQ ID NO 33
<211> LENGTH: 20
<212> TYPE: DNA
<213> ORGANISM: Artificial
<220> FEATURE:
<223> OTHER INFORMATION: forward primer for Homo sapiens peptidylglycine
      alpha-amidating monooxygenase COOH-terminal interactor, mRNA

<400> SEQUENCE: 33
tgatcatttc ccaggaccat                                              20

<210> SEQ ID NO 34
<211> LENGTH: 20
<212> TYPE: DNA
<213> ORGANISM: Artificial
<220> FEATURE:
<223> OTHER INFORMATION: reverse primer for Homo sapiens peptidylglycine
      alpha-amidating monooxygenase COOH-terminal interactor, mRNA

<400> SEQUENCE: 34
cccttccgca tcttcattta                                              20

<210> SEQ ID NO 35
<211> LENGTH: 20
<212> TYPE: DNA
<213> ORGANISM: Artificial
<220> FEATURE:
<223> OTHER INFORMATION: forward primer for Homo sapiens
      phenylethanolamine N-methyltransferase, mRNA

<400> SEQUENCE: 35
gaatgctggc aggataagga                                              20

<210> SEQ ID NO 36
<211> LENGTH: 20
<212> TYPE: DNA
<213> ORGANISM: Artificial
<220> FEATURE:
<223> OTHER INFORMATION: reverse primer for Homo sapiens
      phenylethanolamine N-methyltransferase, mRNA

<400> SEQUENCE: 36
cttgtagcca ctacgcacca                                              20

<210> SEQ ID NO 37
<211> LENGTH: 20
<212> TYPE: DNA
<213> ORGANISM: Artificial
<220> FEATURE:
<223> OTHER INFORMATION: forward primer for Homo sapiens secretoglobin,
      family 3A, member 1, mRNA

<400> SEQUENCE: 37
ctccgctgct gctttcttag                                              20

```
<210> SEQ ID NO 38
<211> LENGTH: 19
<212> TYPE: DNA
<213> ORGANISM: Artificial
<220> FEATURE:
<223> OTHER INFORMATION: reverse primer for Homo sapiens secretoglobin,
      family 3A, member 1, mRNA

<400> SEQUENCE: 38
ccagctcagc cacacactt                                                    19

<210> SEQ ID NO 39
<211> LENGTH: 20
<212> TYPE: DNA
<213> ORGANISM: Artificial
<220> FEATURE:
<223> OTHER INFORMATION: forward primer for Homo sapiens olfactory
      receptor, family 7, subfamily C, member 1, mRNA

<400> SEQUENCE: 39
agctctgtgg actgctggtt                                                   20

<210> SEQ ID NO 40
<211> LENGTH: 20
<212> TYPE: DNA
<213> ORGANISM: Artificial
<220> FEATURE:
<223> OTHER INFORMATION: reverse primer for Homo sapiens olfactory
      receptor, family 7, subfamily C, member 1, mRNA

<400> SEQUENCE: 40
ggacgccagt tgcaaagtat                                                   20

<210> SEQ ID NO 41
<211> LENGTH: 20
<212> TYPE: DNA
<213> ORGANISM: Artificial
<220> FEATURE:
<223> OTHER INFORMATION: reverse primer for Homo sapiens DnaJ homolog,
      subfamily B, member 8 mRNA

<400> SEQUENCE: 41
ccgacaagaa ccctgacaat                                                   20

<210> SEQ ID NO 42
<211> LENGTH: 20
<212> TYPE: DNA
<213> ORGANISM: Artificial
<220> FEATURE:
<223> OTHER INFORMATION: reverse primer for Homo sapiens DnaJ homolog,
      subfamily B, member 8 mRNA

<400> SEQUENCE: 42
aggtggatga gaaggtggtg                                                   20

<210> SEQ ID NO 43
<211> LENGTH: 65
<212> TYPE: DNA
<213> ORGANISM: Artificial
<220> FEATURE:
<223> OTHER INFORMATION: shDNA oligonucleotide for Sox2

<400> SEQUENCE: 43
gatccgccag ctcgcagacc tacatttcaa gagaatgtag gtctgcgagc tggttttttc       60
tagag                                                                   65
```

```
<210> SEQ ID NO 44
<211> LENGTH: 65
<212> TYPE: DNA
<213> ORGANISM: Artificial
<220> FEATURE:
<223> OTHER INFORMATION: shDNA oligonucleotide for Sox2

<400> SEQUENCE: 44
aattctctag aaaaaaccag ctcgcagacc tacattctct gaaatgtag gtctgcgagc    60 tggcg                                                              65

<210> SEQ ID NO 45
<211> LENGTH: 65
<212> TYPE: DNA
<213> ORGANISM: Artificial
<220> FEATURE:
<223> OTHER INFORMATION: shDNA oligonucleotide for EGFP

<400> SEQUENCE: 45
gatccgcaac agccacaacg tctatttcaa gagaatagac gttgtggctg ttgttttttc   60
tagag                                                              65

<210> SEQ ID NO 46
<211> LENGTH: 65
<212> TYPE: DNA
<213> ORGANISM: Artificial
<220> FEATURE:
<223> OTHER INFORMATION: shDNA oligonucleotide for EGFP

<400> SEQUENCE: 46
aattctctag aaaaaacaac agccacaacg tctattctct gaaatagac gttgtggctg   60 ttgcg                                                              65

<210> SEQ ID NO 47
<211> LENGTH: 9
<212> TYPE: PRT
<213> ORGANISM: Artificial
<220> FEATURE:
<223> OTHER INFORMATION: pepitide fragment of SOX2

<400> SEQUENCE: 47

Met Tyr Asn Met Met Glu Thr Glu Leu
1               5

<210> SEQ ID NO 48
<211> LENGTH: 10
<212> TYPE: PRT
<213> ORGANISM: Artificial
<220> FEATURE:
<223> OTHER INFORMATION: peptide fragment of SOX2

<400> SEQUENCE: 48

Val Trp Ser Arg Gly Gln Arg Arg Lys Met
1               5                   10

<210> SEQ ID NO 49
<211> LENGTH: 9
<212> TYPE: PRT
<213> ORGANISM: Artificial
<220> FEATURE:
<223> OTHER INFORMATION: peptide fragment of SOX2

<400> SEQUENCE: 49

Lys Met Ala Gln Glu Asn Pro Lys Met
1               5
```

```
<210> SEQ ID NO 50
<211> LENGTH: 9
<212> TYPE: PRT
<213> ORGANISM: Artificial
<220> FEATURE:
<223> OTHER INFORMATION: peptide fragment of SOX2

<400> SEQUENCE: 50

Pro Phe Ile Asp Glu Ala Lys Arg Leu
1               5

<210> SEQ ID NO 51
<211> LENGTH: 11
<212> TYPE: PRT
<213> ORGANISM: Artificial
<220> FEATURE:
<223> OTHER INFORMATION: peptide fragment of SOX2

<400> SEQUENCE: 51

Lys Tyr Arg Pro Arg Arg Lys Thr Lys Thr Leu
1               5                   10

<210> SEQ ID NO 52
<211> LENGTH: 9
<212> TYPE: PRT
<213> ORGANISM: Artificial
<220> FEATURE:
<223> OTHER INFORMATION: peptide fragment of SOX2

<400> SEQUENCE: 52

Leu Met Lys Lys Asp Lys Tyr Thr Leu
1               5

<210> SEQ ID NO 53
<211> LENGTH: 9
<212> TYPE: PRT
<213> ORGANISM: Artificial
<220> FEATURE:
<223> OTHER INFORMATION: peptide fragment of SOX2

<400> SEQUENCE: 53

Lys Tyr Thr Leu Pro Gly Gly Leu Leu
1               5

<210> SEQ ID NO 54
<211> LENGTH: 9
<212> TYPE: PRT
<213> ORGANISM: Artificial
<220> FEATURE:
<223> OTHER INFORMATION: peptide fragment of SOX2

<400> SEQUENCE: 54

Gly Trp Ser Asn Gly Ser Tyr Ser Met
1               5

<210> SEQ ID NO 55
<211> LENGTH: 9
<212> TYPE: PRT
<213> ORGANISM: Artificial
<220> FEATURE:
<223> OTHER INFORMATION: peptide fragment of SOX2

<400> SEQUENCE: 55

Ser Tyr Ser Met Met Gln Asp Gln Leu
1               5
```

```
<210> SEQ ID NO 56
<211> LENGTH: 10
<212> TYPE: PRT
<213> ORGANISM: Artificial
<220> FEATURE:
<223> OTHER INFORMATION: peptide fragment of SOX2

<400> SEQUENCE: 56

Pro Met His Arg Tyr Asp Val Ser Ala Leu
1               5                   10

<210> SEQ ID NO 57
<211> LENGTH: 9
<212> TYPE: PRT
<213> ORGANISM: Artificial
<220> FEATURE:
<223> OTHER INFORMATION: peptide fragment of SOX2

<400> SEQUENCE: 57

Ser Met Thr Ser Ser Gln Thr Tyr Met
1               5

<210> SEQ ID NO 58
<211> LENGTH: 10
<212> TYPE: PRT
<213> ORGANISM: Artificial
<220> FEATURE:
<223> OTHER INFORMATION: peptide fragment of SOX2

<400> SEQUENCE: 58

Tyr Met Asn Gly Ser Pro Thr Tyr Ser Met
1               5                   10

<210> SEQ ID NO 59
<211> LENGTH: 10
<212> TYPE: PRT
<213> ORGANISM: Artificial
<220> FEATURE:
<223> OTHER INFORMATION: peptide fragment of SOX2

<400> SEQUENCE: 59

Ser Tyr Ser Gln Gln Gly Thr Pro Gly Met
1               5                   10

<210> SEQ ID NO 60
<211> LENGTH: 11
<212> TYPE: PRT
<213> ORGANISM: Artificial
<220> FEATURE:
<223> OTHER INFORMATION: HLA-A24 binding epitope from HIV

<400> SEQUENCE: 60

Arg Tyr Leu Arg Asp Gln Gln Leu Leu Gly Ile
1               5                   10

<210> SEQ ID NO 61
<211> LENGTH: 9
<212> TYPE: PRT
<213> ORGANISM: Artificial
<220> FEATURE:
<223> OTHER INFORMATION: HLA-A24 binding epitope from EBV

<400> SEQUENCE: 61

Thr Tyr Gly Pro Val Phe Met Ser Leu
1               5
```

```
<210> SEQ ID NO 62
<211> LENGTH: 317
<212> TYPE: PRT
<213> ORGANISM: Homo sapiens

<400> SEQUENCE: 62

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
            35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
            100                 105                 110

Arg Arg Lys Thr Lys Thr Leu Met Lys Lys Asp Lys Tyr Thr Leu Pro
        115                 120                 125

Gly Gly Leu Leu Ala Pro Gly Gly Asn Ser Met Ala Ser Gly Val Gly
130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
            180                 185                 190

Gln Met Gln Pro Met His Arg Tyr Asp Val Ser Ala Leu Gln Tyr Asn
        195                 200                 205

Ser Met Thr Ser Ser Gln Thr Tyr Met Asn Gly Ser Pro Thr Tyr Ser
210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
            260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
    290                 295                 300

Gly Thr Ala Ile Asn Gly Thr Leu Pro Leu Ser His Met
305                 310                 315

<210> SEQ ID NO 63
<211> LENGTH: 8
<212> TYPE: PRT
<213> ORGANISM: Artificial
<220> FEATURE:
<223> OTHER INFORMATION: Epitope from OVA

<400> SEQUENCE: 63

Ser Ile Ile Asn Phe Glu Lys Leu
1               5
```

<210> SEQ ID NO 64
<211> LENGTH: 20
<212> TYPE: DNA
<213> ORGANISM: Artificial
<220> FEATURE:
<223> OTHER INFORMATION: forward primer for mouce DNAJB8

<400> SEQUENCE: 64
tgacagatgg agagcaggtg 20

<210> SEQ ID NO 65
<211> LENGTH: 20
<212> TYPE: DNA
<213> ORGANISM: Artificial
<220> FEATURE:
<223> OTHER INFORMATION: reverse primer for mouce DNAJB8

<400> SEQUENCE: 65
ccctcatgag cttctccttg 20

<210> SEQ ID NO 66
<211> LENGTH: 20
<212> TYPE: DNA
<213> ORGANISM: Artificial
<220> FEATURE:
<223> OTHER INFORMATION: forward primer for G3PDH

<400> SEQUENCE: 66
accacagtcc atgccatcac 20

<210> SEQ ID NO 67
<211> LENGTH: 20
<212> TYPE: DNA
<213> ORGANISM: Artificial
<220> FEATURE:
<223> OTHER INFORMATION: reverse primer for G3PDH

<400> SEQUENCE: 67
tccaccaccc tgttgctgta 20

<210> SEQ ID NO 68
<211> LENGTH: 9
<212> TYPE: PRT
<213> ORGANISM: Artificial
<220> FEATURE:
<223> OTHER INFORMATION: peptide fragment of DNAJB8

<400> SEQUENCE: 68

Ala Tyr Arg Lys Leu Ala Leu Arg Trp
1               5

<210> SEQ ID NO 69
<211> LENGTH: 10
<212> TYPE: PRT
<213> ORGANISM: Artificial
<220> FEATURE:
<223> OTHER INFORMATION: peptide fragment of DNAJB8

<400> SEQUENCE: 69

Gly Tyr Thr Phe Arg Asn Pro Glu Asp Ile
1               5                   10

<210> SEQ ID NO 70
<211> LENGTH: 9
<212> TYPE: PRT
<213> ORGANISM: Artificial

```
<220> FEATURE:
<223> OTHER INFORMATION: peptide fragment of DNAJB8

<400> SEQUENCE: 70

Ile Phe Arg Glu Phe Phe Gly Gly Leu
1               5

<210> SEQ ID NO 71
<211> LENGTH: 9
<212> TYPE: PRT
<213> ORGANISM: Artificial
<220> FEATURE:
<223> OTHER INFORMATION: peptide fragment of DNAJB8

<400> SEQUENCE: 71

Ala Phe Met Glu Ala Phe Ser Ser Phe
1               5

<210> SEQ ID NO 72
<211> LENGTH: 9
<212> TYPE: PRT
<213> ORGANISM: Artificial
<220> FEATURE:
<223> OTHER INFORMATION: peptide fragment of survivin

<400> SEQUENCE: 72

Ala Tyr Ala Cys Asn Thr Ser Thr Leu
1               5

<210> SEQ ID NO 73
<211> LENGTH: 10
<212> TYPE: PRT
<213> ORGANISM: Artificial
<220> FEATURE:
<223> OTHER INFORMATION: peptide fragment of OR7C1

<400> SEQUENCE: 73

Met Tyr Leu Val Thr Phe Thr Gly Asn Leu
1               5                   10

<210> SEQ ID NO 74
<211> LENGTH: 10
<212> TYPE: PRT
<213> ORGANISM: Artificial
<220> FEATURE:
<223> OTHER INFORMATION: peptide fragment of OR7C1

<400> SEQUENCE: 74

Met Tyr Phe Phe Leu Ser Asn Leu Ser Phe
1               5                   10

<210> SEQ ID NO 75
<211> LENGTH: 10
<212> TYPE: PRT
<213> ORGANISM: Artificial
<220> FEATURE:
<223> OTHER INFORMATION: peptide fragment of OR7C1

<400> SEQUENCE: 75

Thr Tyr Ala Gly Cys Leu Ser Gln Ile Phe
1               5                   10

<210> SEQ ID NO 76
<211> LENGTH: 10
<212> TYPE: PRT
<213> ORGANISM: Artificial
```

<220> FEATURE:
<223> OTHER INFORMATION: peptide fragment of OR7C1

<400> SEQUENCE: 76

His Tyr Thr Val Ile Met Asn Pro Gln Leu
1               5                   10

<210> SEQ ID NO 77
<211> LENGTH: 10
<212> TYPE: PRT
<213> ORGANISM: Artificial
<220> FEATURE:
<223> OTHER INFORMATION: peptide fragment of OR7C1

<400> SEQUENCE: 77

Ser Tyr Tyr Lys Ile Val Phe Ser Ile Leu
1               5                   10

<210> SEQ ID NO 78
<211> LENGTH: 10
<212> TYPE: PRT
<213> ORGANISM: Artificial
<220> FEATURE:
<223> OTHER INFORMATION: peptide fragment of OR7C1

<400> SEQUENCE: 78

Phe Tyr Gly Thr Gly Phe Gly Val Tyr Leu
1               5                   10

<210> SEQ ID NO 79
<211> LENGTH: 9
<212> TYPE: PRT
<213> ORGANISM: Artificial
<220> FEATURE:
<223> OTHER INFORMATION: peptide fragment of OR7C1

<400> SEQUENCE: 79

Met Tyr Thr Met Val Thr Pro Met Leu
1               5

<210> SEQ ID NO 80
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 80
atggagacag acacactcct gctatgggta ctgctgctct gggttccagg ttccactggt    60
gac                                                                 63

<210> SEQ ID NO 81
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 81
gattacaagg atgacgacga taag                                          24